United States Patent
Chakravarty et al.

[11] Patent Number: 5,441,959
[45] Date of Patent: * Aug. 15, 1995

[54] SUBSTITUTED QUINAZOLINONES BEARING ACIDIC FUNCTIONAL GROUPS AS ANGIOTENSIN II ANTAGONISTS

[75] Inventors: Prasun K. Chakravarty, Edison; Stephen E. de Laszlo, Atlantic Highlands; Tomasz W. Glinka, Westfield; William J. Greenlee, Teaneck, all of N.J.; Nathan B. Mantlo, Ledyard, Conn.; Arthur A. Patchett, Westfield, N.J.

[73] Assignee: Merck & Co., Inc., Rahway, N.J.

[*] Notice: The portion of the term of this patent subsequent to Aug. 24, 2010 has been disclaimed.

[21] Appl. No.: 108,465

[22] Filed: Aug. 18, 1993

Related U.S. Application Data

[63] Continuation-in-part of Ser. No. 867,794, Apr. 16, 1992, Pat. No. 5,238,942, which is a continuation-in-part of Ser. No. 698,506, May 10, 1991, abandoned.

[51] Int. Cl.6 .................. A61K 31/505; C07D 239/72; C07D 239/90
[52] U.S. Cl. ............................... 514/259; 514/234.5; 514/234.8; 514/116; 514/119; 514/287; 514/290
[58] Field of Search ............................ 514/234.5, 259; 544/116, 119, 287, 290

[56] References Cited

U.S. PATENT DOCUMENTS

| | | | |
|---|---|---|---|
| 5,238,942 | 8/1993 | Chakravarty et al. | 514/259 |
| 5,238,942 | 8/1993 | Chakravarty et al. | 514/259 |
| 5,240,928 | 8/1993 | Allen et al. | 514/259 |

FOREIGN PATENT DOCUMENTS

| | | |
|---|---|---|
| 58696/90 | 7/1990 | Australia . |
| 407342 | 6/1990 | European Pat. Off. . |
| 411766 | 6/1990 | European Pat. Off. . |

*Primary Examiner*—Yogendra N. Gupta
*Attorney, Agent, or Firm*—Elliot Korsen; Mark R. Daniel; Joseph F. DiPrima

[57] ABSTRACT

Novel substituted quinazolinones of the formula (I) are useful as angiotensin II antagonists.

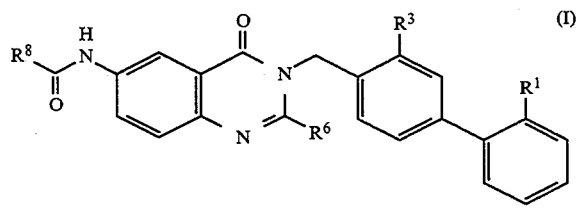

12 Claims, No Drawings

SUBSTITUTED QUINAZOLINONES BEARING ACIDIC FUNCTIONAL GROUPS AS ANGIOTENSIN II ANTAGONISTS

RELATED APPLICATION

The present patent application is a continuation-in-part of application Ser. No. 07/867,794, filed 16 Apr. 1992, U.S. Pat. No. 5,238,942, which is a continuation-in-part of Ser. No. 698,506, filed 10 May 1991, now abandoned.

INTRODUCTION OF THE INVENTION

This invention relates to novel substituted quinazolinone compounds and derivatives thereof which are useful as angiotensin II antagonists in the treatment of elevated blood pressure and congestive heart failure. The substituted quinazolinone compounds of the invention are also useful to reduce elevated intraocular pressure and to inhibit restenosis.

It also relates to processes for preparing the novel compounds; pharmaceutical formulations comprising one or more of the compounds as active ingredient; and, a method of treatment of hypertension, congestive heart failure, and elevated intraocular pressure.

The compounds of this invention also have central nervous sytem (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

BACKGROUND OF THE INVENTION

The renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by their partial agonist activity and lack of oral absorption [M. Antonaccio. Clin. Exp. Hypertens. A4, 27–46 (1982); D. H. P. Streeten and G. H. Anderson, Jr.—Handbook of Hypertension, Clinical Pharmacology of Antihypertensive Drugs, ed. A. E. Doyle, Vol. 5, pp. 246–271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324; 4,340,598; 4,576,958; 4,582,847 and 4,880,804 in European Patent Applications 028,834; 245,637; 253,310; 291,969; 392,317; 399,731; 403,158; 403,159; 407,342; 411,507; 412,848; and 415,886; and in articles by A. T. Chiu, et al. [Eur. J. Pharm. Exp. Therap, 157, 13–21 (1988)] and by P. C. Wong, et al. [J, Pharm, Exp. Therap, 247, 1–7(1988), Hypertension, 13, 489–497 (1989)]. European Patent Applications 028,834 and 253,310 and the above three articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

DETAILED DESCRIPTION OF THE INVENTION

This invention relates to novel substituted quinazolinone compounds and derivatives thereof which are useful as angiotensin II antagonists, primarily as antihypertensives. The compounds of this invention have the general formula (I):

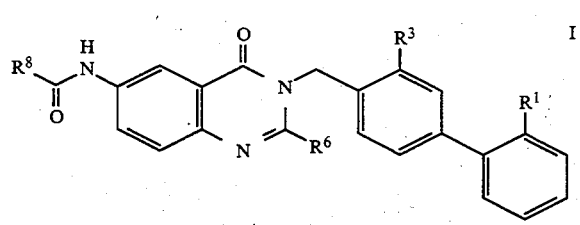

or a pharmaceutically acceptable salt thereof, wherein:
$R^1$ is $-SO_2NHCO_2R^{23}$;
$R^3$ is
(a) halogen (Cl, Br, I, F),
(b) $C_1-C_4$ alkyl, or
(c) $CF_3$;
$R^6$ is straight chain $C_1-C_4$ alkyl;
$R^8$ is
(a) $R^{23'}$
(b) $NR^{24}R^{23'}$;
$R^{23}$ and $R^{23'}$ are independently
(a) aryl, wherein aryl is defined as phenyl or naphthyl unsubstituted or substituted with one or two substituents selected from the group consisting of: halogen (Cl, Br, I, F), $N(R^{24})_2$, $CO_2R^{24}$, $C_1-C_4$ alkyl, $C_1-C_4$ alkoxyl, $NO_2$, $CF_3$, $C_1-C_4$ alkylthio, OH, $-SO_2N(R^{24})_2$, $C_3-C_7$ cycloalkyl, $C_3-C_{10}$ alkenyl and $S(O)_n(C_1-C_4$ alkyl); where $n=1$ or 2,
(b) heteroaryl, wherein heteroaryl is an unsubstituted or mono or disubstituted heteroaromatic 5- or 6-membered ring which can contain one or two heteroatoms selected from the group consisting of N, O and S and wherein the substituents are members selected from the group consisting of $-OH$, $-SH$, $C_1-C_4$ alkyl, $C_1-C_4$ alkoxy, $CF_3$, halogen (Cl, Br, I, F) and $NO_2$,
(c) $C_3-C_7$ cycloalkyl,
(d) $C_1-C_6$ alkyl optionally substituted with a substituent selected from the group consisting of aryl as defined above, heteroaryl as defined above, $-OH$, $-SH$, $C_1-C_4$ alkyl, $-O(C_1-C_4$ alkyl), $C_3-C_7$ cycloalkyl, $-S(O)_n(C_1-C_4$ alkyl), $-CF_3$, halogen (Cl, Br, F, I), $-NO_2$, $-CO_2H$, $CO_2$-$C_1$-$C_4$-alkyl, —$NH_2$, —$NH(C_1$-$C_4$ alkyl), —$N(C_1$-$C_4$ alkyl)$_2$, or (e) perfluoro-$C_1$-$C_4$ alkyl; and $R^{24}$ is (a) H, (b) $C_1$-$C_6$ alkyl, unsubstituted or substituted with aryl as defined above or heteroaryl as defined above, or (c) aryl; and $R^{23'}$ and $R^{24}$ when taken together may form a morpholine or piperazine ring, wherein the piperazine ring may be substituted on the nitrogen with $C_1$-$C_4$ alkyl or $C_1$-$C_4$ acyl.

One embodiment of the compounds of Formula 1 are those wherein

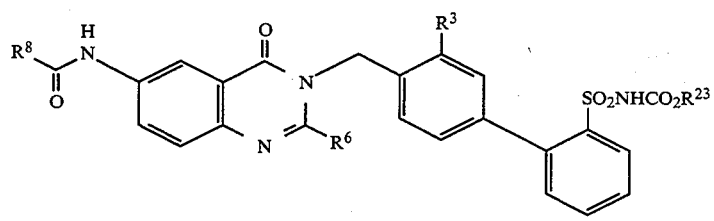

$R^3$ is (a) F, (b) Me, or (c) $CF_3$;

$R^6$ is straight chain $C_1$-$C_4$ alkyl;

$R^8$ is $R^{23'}$;

$R^{23'}$ is (a) aryl, wherein aryl is defined as phenyl or naphthyl unsubstituted or substituted with one or two substituents selected from the group consisting of: halogen (Cl, Br, I, F), $N(R^{24})_2$, $CO_2R^{24}$, $C_1$-$C_4$ alkyl, $C_1$-$C_4$ alkoxyl, $NO_2$, $CF_3$, $C_1$-$C_4$ alkylthio, OH, —$SO_2N(R^{24})_2$, $C_3$-$C_7$ cycloalkyl, $C_3$-$C_{10}$ alkenyl and $S(O)_n(C_1$-$C_4$ alkyl); where n=1 or 2, (b) heteroaryl, wherein heteroaryl is an unsubstituted or mono- or disubstituted heteroaromatic 5- or 6-membered ring which can contain one or two heteroatoms selected from the group consisting of N, O and S and Wherein the substituents are members selected from the group consisting of —OH, —SH, $C_1$-$C_4$ alkyl, $C_1$-$C_4$ alkoxy, $CF_3$, halogen (Cl, Br, I, F) and $NO_2$, (c) $C_1$-$C_6$ alkyl unsubstituted or substituted with a substituent selected from the group consisting of aryl as defined above, heteroaryl as defined above, —OH, —SH, $C_1$-$C_4$ alkyl, —$O(C_1$-$C_4$ alkyl), $C_3$-$C_7$ cycloalkyl, —$CF_3$, halogen (Cl, Br, F, I), —$N(C_1$-$C_4$ alkyl)$_2$, or $C_3$-$C_7$ cycloalkyl; and $R^{23}$ is (a) $C_1$-$C_6$-alkyl, unsubstituted or substituted with a substituent selected from the group consisting of:

aryl as defined above, heteroaryl as defined above, $C_1$-$C_4$ alkyl, $CF_3$, —$O(C_1$-$C_4$ alkyl), $C_3$-$C_7$ cycloalkyl, or (b) perfluoro-$C_1$-$C_4$-alkyl.

This embodiment is exemplified further by:

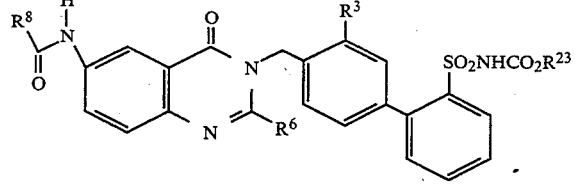

| $R^{23}$ | $R^3$ | $R^6$ | $R^8$ |
|---|---|---|---|
| iPn | F | Pr | Ph |
| iPn | F | Pr | -2-furoyl |
| iPn | F | Bu | Et |
| iPn | F | Bu | Pr |
| iPn | F | Pr | $CH_2OCH_2CH_3$ |
| iPn | F | Et | -2-furoyl |
| iPn | F | Et | Ph |
| iPn | F | Et | -3-pyridyl |
| iPn | F | Et | -4-pyridyl |
| iPn | F | Et | -2-pyridyl |
| $(CH_2)_2cPr$ | F | Et | Ph |
| $(CH_2)_2cPr$ | F | Et | -2-furoyl | wherein

Et is ethyl,

Pr is n-propyl, cPr is cyclopropyl,

Bu is n-butyl, iPn is 3-methylbutyl,

Ph is phenyl.

A second embodiment of structures of Formula I are those wherein $R^{23}$, $R^3$, $R^6$ are as recited in the first embodiment and all other substituents are as recited below:

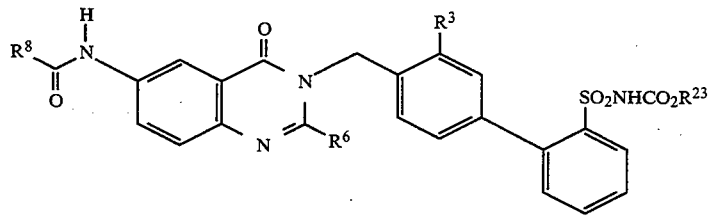

$R^8$ is —$NR^{24}R^{23'}$;

$R^{23'}$ is $C_1$-$C_6$ alkyl which is unsubstituted or substituted with a substituent selected from the group aryl, heteroaryl, $C_1$-$C_4$ alkyl, —$O(C_1$-$C_4$ alkyl), $CF_3$, $NH(C_1$-$C_4$ alkyl), $N(C_1$-$C_4$ alkyl)$_2$, $C_3$-$C_7$ cycloalkyl;

$R^{24}$ is (a) $C_1$-$C_6$ alkyl which is unsubstituted or substituted with aryl or heteroaryl, or
(b) H; and $R^{23'}$ and $R^{24}$ when taken together may form a morpholine- or piperazine ring, wherein the piperazine ring may be substituted on the nitrogen with $C_1$-$C_4$ alkyl or $C_1$-$C_4$ acyl.

Compounds exemplifying this embodiment include:

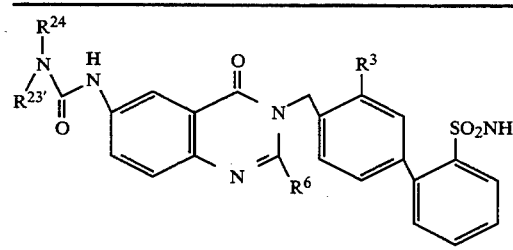

| $R^{23}$ | $R^3$ | $R^6$ | $R^{23'}$ | $R^{24}$ |
|---|---|---|---|---|
| iPn | Me | Pr | iPr | H |
| Bu | Me | Pr | iPr | H |
| Bu | F | Pr | iPr | H |
| iPn | F | Pr | iPr | H |
| iPn | Me | Pr | iPr | H |
| Bu | F | Bu | iPr | Me |
| iPn | F | Pr | iPr | H |
| (CH$_2$)$_2$cPr | F | Bu | iPr | Me |
| (CH$_2$)$_2$cPr | F | Et | Et | H |
| Me | F | Et | Et | H |
| iPn | F | Pr | morpholino | |
| iPn | F | Bu | iPr | Me |
| iPn | F | Et | iPr | Me |
| iPn | F | Et | morpholino | |
| Bu | F | Et | morpholino | |
| iPn | F | Bu | piperazinyl-4-methyl | |
| Bu | F | Et | iPr | Me |
| (CH$_2$)$_2$tBu | F | Pr | iPr | H |
| tBu | F | Pr | iPr | H |
| iPr | F | Pr | Me | Me |
| iHx | F | Et | morpholino | |
| iPn | F | Et | Me | Me |
| (CH$_2$)$_2$cPr | F | Et | iPr | H |
| (CH$_2$)$_2$cPr | F | Et | iPr | Me |
| iPn | F | Me | iPr | H |
| iPn | F | Me | iPr | Me |
| (CH$_2$)$_2$cPr | F | Me | Me | Me |
| iBu | F | Et | iPr | Me |
| iPn | F | Et | iPr | Me | wherein
Me is methyl,
Et is ethyl,
Pr is n-propyl,
cPr is cyclopropyl,
iPr is isopropyl,
Bu is n-butyl,
iBu is isobutyl,
tBu is t-butyl,
iPn is 3-methylbutyl,
iHx is 4-methylpentyl.

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

The heteroaryl substituent recited above represents any 5 or 6-membered aromatic ring containing from one to three heteroatoms selected from the group consisting of nitrogen, oxygen, and sulfur, for example, pyridyl, thienyl, furyl, pyrazolyl, pyrrolyl, imidazolyl, pyridazinyl, pyrimidinyl, pyrazinyl, isoxazolyl, isothiazolyl, oxazolyl, triazolyl and thiazolyl.

| ABBREVIATIONS USED IN SCHEMES | |
|---|---|
| DMAP | Dimethylaminopyridine |
| -OTs | p-toluenesulphonate |
| -OTf | Trifluoromethanesulfonate |
| DMF | Dimethylformamide |
| DBU | 1,8-Diazabicyclo[5.4.0]undecane |
| FAB MS | Fast Atom bombardment mass spectroscopy |
| THF | Tetrahydrofuran |
| DMSO | Dimethylsulfoxide |
| EtAc | Ethyl acetate |
| HOAc | Acetic Acid |
| TFA | Trifluoroacetic acid. |

Compounds of Formula 1 may be prepared as described in the Schemes illustrated below:

Scheme 1 illustrates the preparation of 6-nitro quinazolin-4(3H)-ones. The appropriately substituted anthranilonitrile is acylated using the requisite acyl chloride to give 2 then cyclized in the presence of basic hydrogen peroxide to give 3.

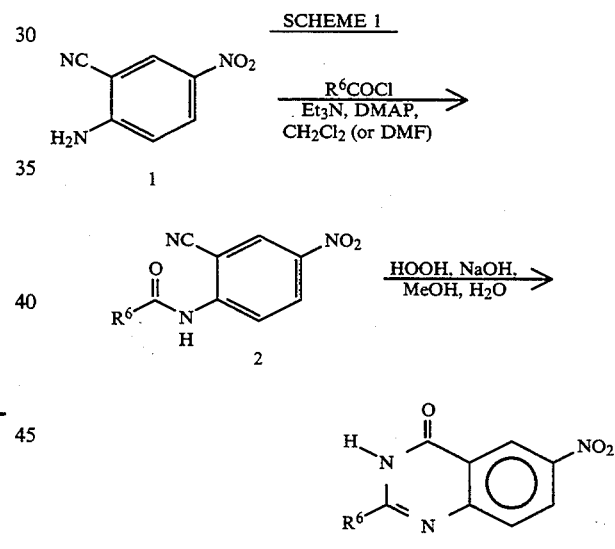

SCHEME 1

Scheme 2 shows an alternate preparation of 2-substituted quinazolin-4(3H)-ones (3) starting with the corresponding anthranilic acid. 2-amino-5-nitro anthranilic acid is treated with two equivalents of the requisite acyl chloride in DMF with triethylamine and DMAP at 0° C. This is then heated to 110° C. for two hours after which time excess ammonium carbonate is added.[2]

SCHEME 2

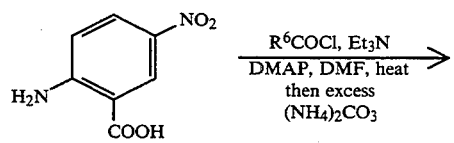

-continued
SCHEME 2

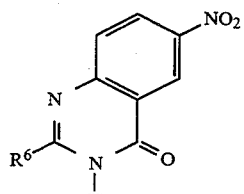

schemes that the 4-bromo-2-fluoro-toluene can be replaced with the coresponding 4-bromo-2-alkyl-toluene, 4-bromo-2-halo-toluene or 4-bromo-2-trifluoro-toluene to obtain the other $R^3$ substituents decribed in the disclosure. Alternatively, the quinazolinone 3 may be alkylated under standard conditions with 4-bromo-2-fluoro-bromomethylbenzene to provide the intermediate 6 that may then be coupled with boronic acid A to give 5.

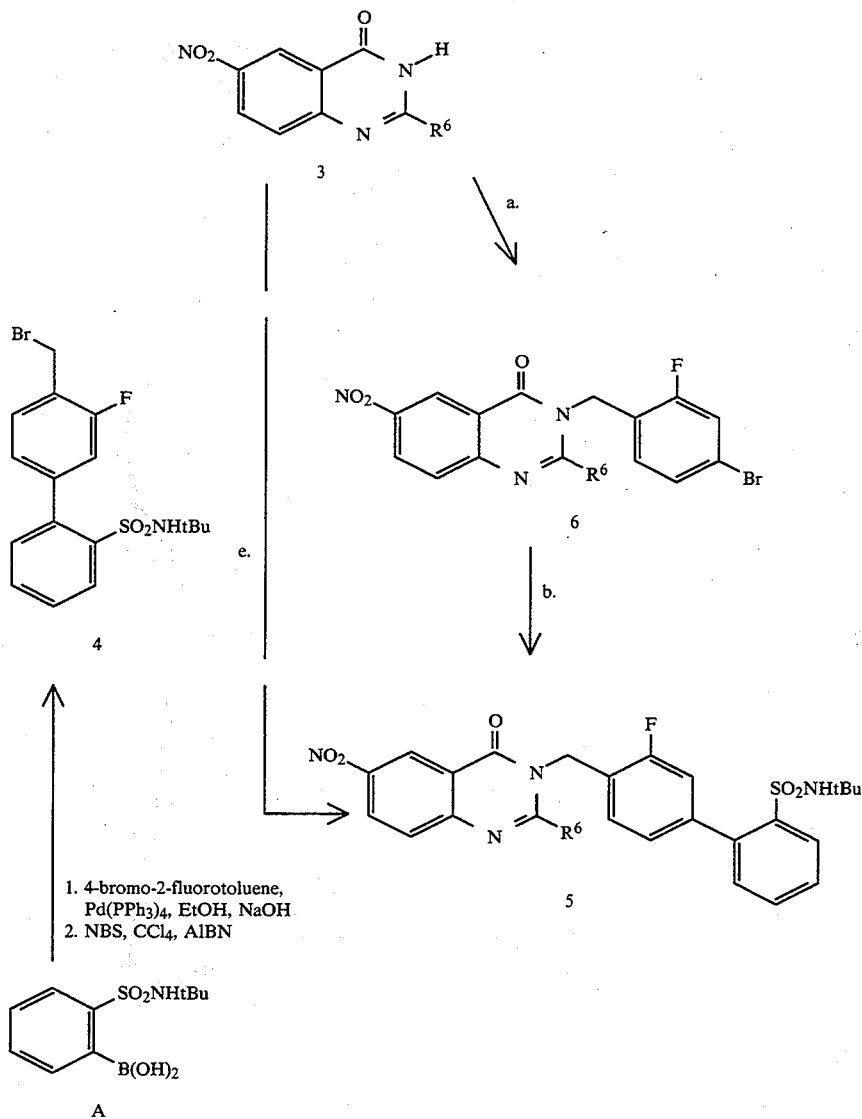

Scheme 3 outlines the preparation of 3-substituted quinazolinone precursors of compounds of Formula I. The 6-nitro-quinazolinone 3 may be alkylated with either the bromomethylbiphenyl 4 (prepared by coupling of the boronic acid A to 4-bromo-2-fluoro-toluene followed by free radical halogenation of the methyl group (NBS/AIBN)) to give directly a precursor 5 to compounds of Formula I. It should be noted, throughout the Scheme 4 outlines synthetic approaches to the 6-acylamino quinazolinones that are useful precursors to compounds of Formula I. 6-Nitro-quinazolinones 3 may be reduced ($H_2$ 10% Pd/C) to 6-amino-quinazolinones and then acylated under standard conditions to provide 6-amido or 6-urea substituted quinazolinones 7. These may in mm be alkylated (and coupled) as in Scheme 3 to provide 8. Alternatively, the 6-nitro-quinazolinone intermediate 5 may be reduced and acylated to give 8 directly.

SCHEME 4

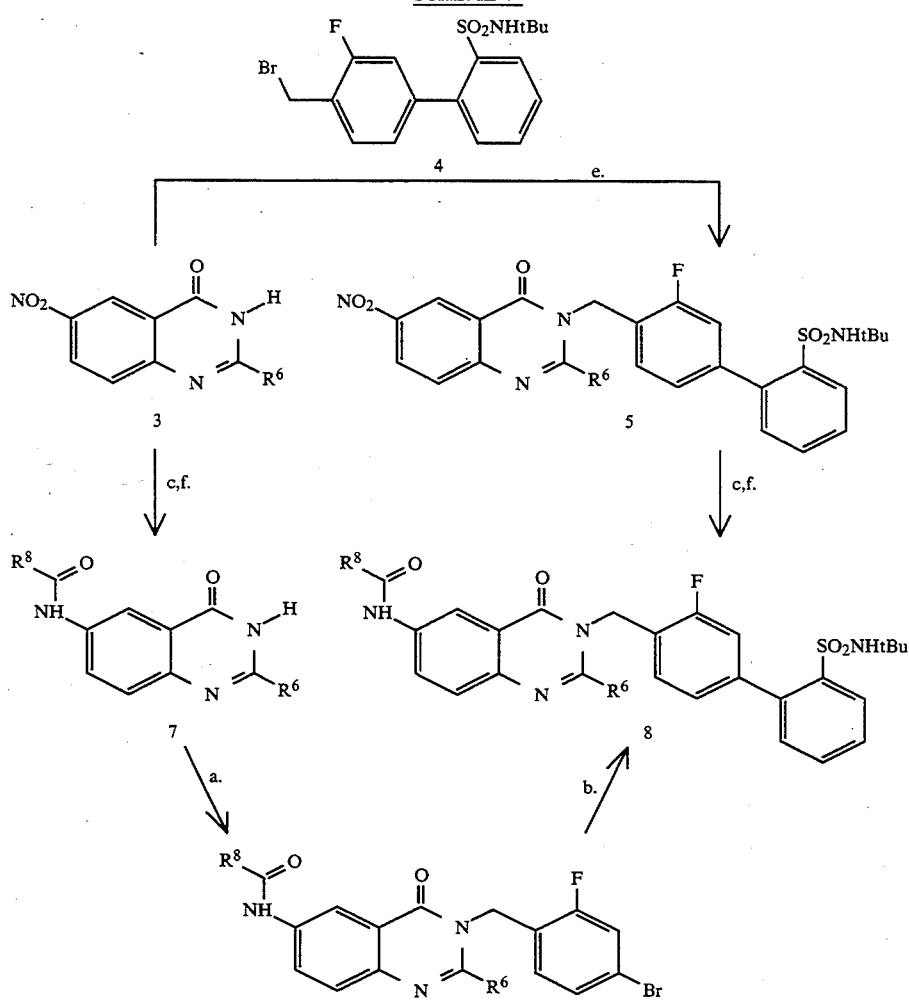

Scheme 5 illustrates some methods employed to prepare the sulfonyl carbamate substituted biphenyl system. The 6-acylamino or urea substituted quinazolinone 8 may be treated with an acid such as trifluoroacetic acid to give the sulfonamide 9. The sulfonamide may then be acylated with the chloroformate of choice to give compounds of Formula I. If it is necessary to convert the urea R²³ or R²⁴ group to a different substituent, heating with the amine of choice neat or in the presence of pyridine will provide the new urea 10. This compound may, in turn, be acylated with a chloroformate to give 1.

SCHEME 5

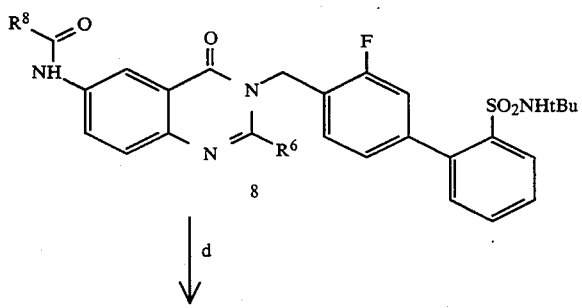

SCHEME 5

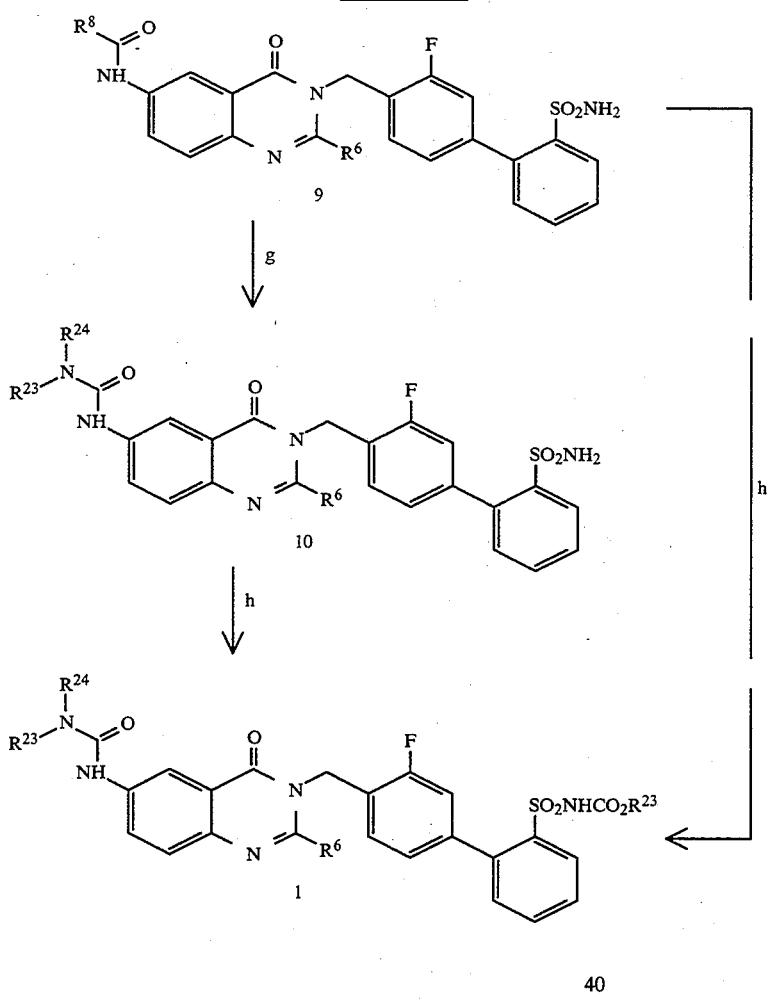

Scheme 6 illustrates a further route to compounds of Formula I employing an alternative sequence of steps from intermediate 5 by deprotecting the sulfonamide by treatment with acid to give 11. Acylation of the sulfonamide with a chloroformate provides intermediate 12 which may then be reduced by hydrogenation over Pd/C to give the aniline 13. Acylation of the amine with acyl halides, isocyanates or phosgene (or triphosgene) and amines will provide compounds of Formula I.

SCHEME 6

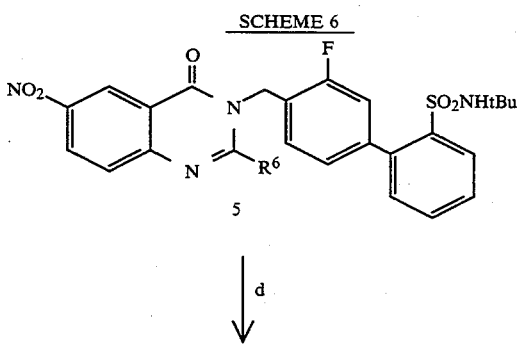

-continued
SCHEME 6

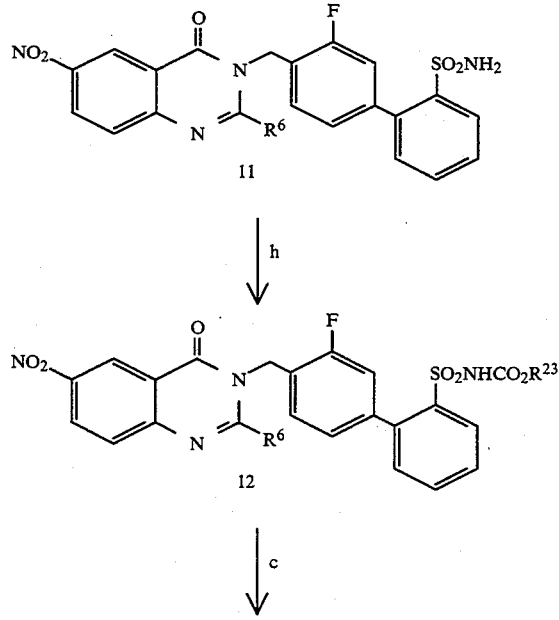

-continued
SCHEME 6

SCHEME 7

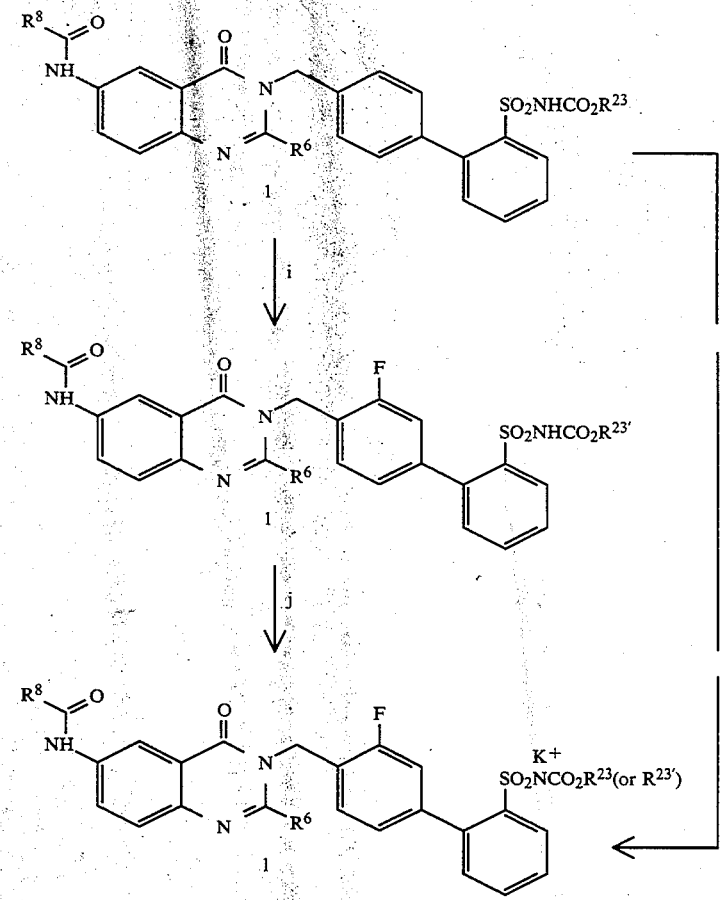

1 in a solvent such as methanol with one equivalent of potassium hydroxide.

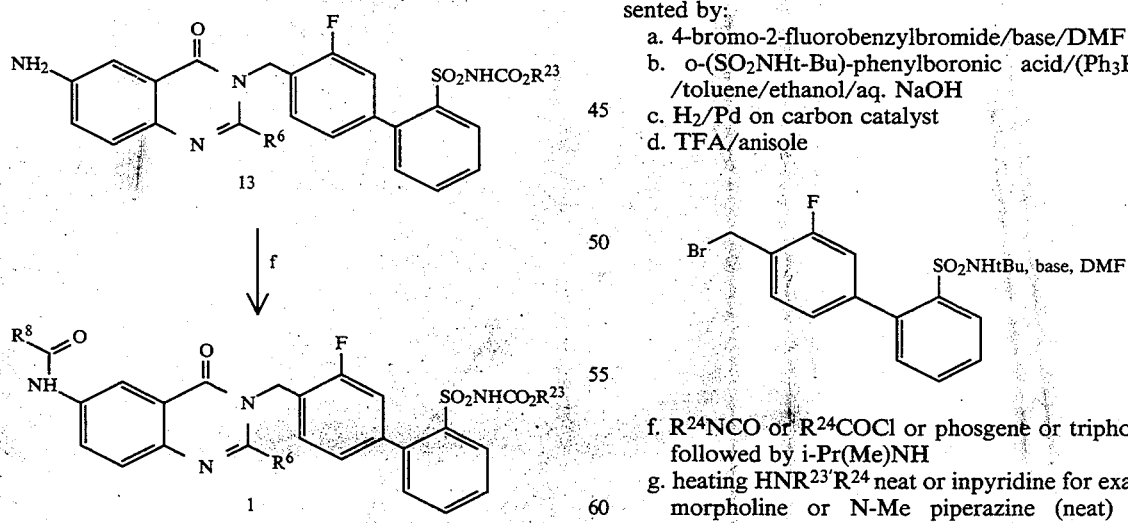

Scheme 7 outlines how the carbamate group may be exchanged thereby altering $R^{23}$. Some analogues of compounds of Formula I may be prepared by heating a compound of Formula I in an alcohol of choice ($R^{23'}$OH) thereby exchanging the $R^{23}$ for $R^{23'}$. Salts of compounds of Formula I, of which the potassium salt is an Example, may be prepared by treating a solution of The reagents utilized in the schemes above are represented by:
a. 4-bromo-2-fluorobenzylbromide/base/DMF
b. o-($SO_2$NHt-Bu)-phenylboronic acid/$(Ph_3P)_4$Pd-/toluene/ethanol/aq. NaOH
c. $H_2$/Pd on carbon catalyst
d. TFA/anisole f. $R^{24}$NCO or $R^{24}$COCl or phosgene or triphosgene followed by i-Pr(Me)NH
g. heating $HNR^{23'}R^{24}$ neat or in pyridine for example: morpholine or N-Me piperazine (neat) or i-Pr(Me)NH/pyridine
h. $R^{23'}$OCOCl/DMAP/pyridine
i. heating in $R^{23'}$OH (neat)
j. KOH/MeOH/$Et_2O$ It will be recognized by those skilled in the art that other reagents may be substituted for those shown above providing they are compatible with the structures shown.

It will be appreciated by those skilled in the art that functional group transformations can be conducted on aryl and heterocyclic rings to afford desired analogs. For example, esters may be converted to amides by heating them with amines and an amid nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluene-sulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. In order to identify AII antagonists and determine their efficacy in vitro, the following two ligand-receptor binding assays were established.

Receptor Binding Assay Using Rabbit Aortae Membrane Preparation;

Three frozen rabbit aortae (obtained from Pel-Freeze Biologicals) are suspended in 5 mM Tris-0.25M Sucrose, pH 7.4 buffer (50 ml) homogenized, and then centrifuged. The mixture is filtered through a cheesecloth and the supernatant is centrifuged for 30 minutes at 20,000 rpm at 4° C. The pellet thus obtained is resuspended in 30 ml of 50 mM Tris-5 mM $MgCl_2$ buffer containing 0.2% Bovine Serum Albumin and 0.2 mg/ml Bacitration and the suspension is used for 100 assay tubes. Samples tested for screening are done in duplicate. To the membrane preparation (0.25 ml) there is added $^{125}$I-Sar$^1$Ile$^8$-angiotensin II [obtained from New England Nuclear] (10 ul; 20,000 cpm) with or without the test sample and the mixture is incubated at 37° C. for 90 minutes. The mixture is then diluted with ice-cold 50 mM Tris-0.9% NaCl, pH 7.4 (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration ($IC_{50}$) of a potential AII antagonist which gives 50% displacement of the total specifically bound $^{125}$I-Sar$^1$Ile$^8$-angiotensin II is presented as a measure of the efficacy of such compounds as AII antagonists.

Receptor Assay Using Bovine Adrenal Cortex Preparation

Bovine adrenal cortex is selected as the source of AII receptor. Weighed tissue (0.1 g is needed for 100 assay tubes) is suspended in Tris.HCl (50 mM), pH 7.7 buffer and homogenized. The homogenate is centrifuged at 20,000 rpm for 15 minutes. Supernatant is discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there is added 3H-angiotensin II (50 mM) (10 ul) with or without the test sample and the mixture is incubated at 37° C. for 1 hour. The mixture is then diluted with Tris buffer (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration ($IC_{50}$) of a potential AII antagonist which gives 50% displacement of the total specifically bound $^3$H-angiotensin II is presented as a measure of the efficacy of such compounds as AII antagonists.

Receptor Assay Using Rat Brain Membrane Preparation

Membranes from rat brain (thalamus, hypothalamus and midbrain) are prepared by homogenization in 50 mM Tris HCl (pH 7.4), and centrifuged at 50,000× g. The resulting pellets are washed twice in 100 mM NACl, 5 mM $Na_2$.EDTA, 10 mM $Na_2HPO_4$ (pH 7.4) and 0.1 mM PMSF by resuspension and centrifugation. For binding assays, the pellets are resuspended in 160 volumes of binding assay buffer (100 mM NaCl, 10 mM $Na_2HPO_4$, 5 mM $Na_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$,Ile$^8$-angiotensin II (1 μM) (for nonspecific binding) or test compounds (for displacement) and 10 μl of [$^{125}$I]Sar$^1$-,Ile$^8$-angiotensin II (23–46 pM) are added to duplicate tubes. The receptor membrane preparation (500 μl) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters is counted using a gamma counter.

Using the methodology described above, representative compounds of this invention could be evaluated and an $IC_{50} < 50$ μM determined, thereby demonstrating and confirming the utility of the compounds of the invention as effective A II antagonists.

The antihypertensive effects of the compounds described in the present invention may be evaluated using the methodology described below:

Male Charles River Sprague-Dawley rats (300–375 gm) are anesthetized with methohexital (Brevital; 50 mg/kg i.p.) and the trachea is cannulated with PE 205 tubing. A stainless steel pithing rod (1.5 mm thick, 150 mm long) is inserted into the orbit of the right eye and down the spinal column. The rats are immediately placed on a Harvard Rodent Ventilator (rate—60 strokes per minute, volumn—1.1 cc per 100 grams body weight). The right carotid artery is ligated, both left and right vagal nerves are cut, and the left carotid artery is cannulated with PE 50 tubing for drug administration, and body temperature is maintained at 37° C. by a thermostatically controlled heating pad which received input from a rectal temperature probe. Atropine (1 mg/kg i.v.) is then administered, and 15 minutes later propranolol (1 mg/kg i.v.). Thirty minutes later antagonists of formula I are administered intravenously or orally. Angiotensin II is then typically given at 5, 10, 15, 30, 45 and 60 minute intervals and every half-hour thereafter for as long as the test compound showed activity. The change in the mean arterial blood pressure is recorded for each angiotensin II challenge and the precent inhibition of the angiotensin II response is calculated.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 5 to 150 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage uniform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are-not to be considered as limiting the invention set forth in the claims appended hereto. All $^1$H-NMR spectra were recorded on a Varian XL-300 Fourier transform spectrometer. Chemical shifts are reported as (parts per million) downfield from tetramethyl silane. Mass spectra were obtained from the Merck and Co. mass spectral facility in Rahway N.J. Analytical TLC was conducted on E. M. Merck precoated silica plates (0.25 mm in glass, Kieselgel 60 $F_{254}$) with UV visualization. All chromatography was conducted on E. M. Merck silica gel. All reactions were carded out under an atmosphere of dry nitrogen under standard conditions for those skilled in the art.

By utilizing the reaction conditions described in the Examples below in sequences indicated by the Methods A, B, C, D, E, F, G, H, I the compounds in the Table below, amongst others, were prepared:

TABLE 1

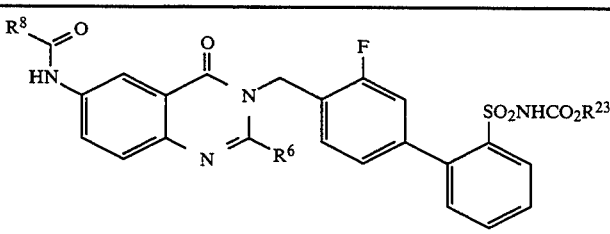

| Compound # | $R^6$ | $R^8$ | $R^{23}$ | Method | FAB MS m/e |
|---|---|---|---|---|---|
| 1 | Me | —NHiPr | 3-methylbutyl | B | 638.0 |
| 2 | Me | —N(Me)iPr | 3-methylbutyl | E | 651.8 |
| 3 | Me | —N(Me)$_2$ | 2-cyclopropylethyl | E | 622.1 |
| 4 | Et | —NHEt | 2-cyclopropylethyl | C = c,f,a,b,d,h | 636.3 |
| 5 | Et | —NHEt | methyl | D = c,f,a,b,d,h,i | 582.7 |
| 6 | Et | —N(Me)iPr | 3-methylbutyl | H = e,d,c,f,h | 666.0 |
| 7 | Et | —N(CH$_2$CH$_2$)$_2$O | 3-methylbutyl | B | 680.3 |
| 8 | Et | —N(CH$_2$CH$_2$)$_2$O | n-butyl | G = c,f,a,b,d,g,h,i | 666.3 |
| 9 | Et | —N(Me)iPr | n-butyl | H | 652.0 |
| 10 | Et | —N(CH$_2$CH$_2$)$_2$O | 4-methylpentyl | B | 694.1 |
| 11 | Et | —N(Me)$_2$ | 3-methylbutyl | E = c,f,e,d,g,h | 637.9 |
| 12 | Et | —NHiPr | 2-cyclopropylethyl | F = c,f,e,d,h | 649.9 |
| 13 | Et | —N(Me)iPr | 2-cyclopropylethyl | H | 664.0 |
| 14 | Et | Ph | 3-methylbutyl | I = e,d,h,c,f | 671.2 |
| 15 | Et | 3-Pyr | 3-methylbutyl | I | 672.2 |
| 16 | Et | 4-Pyr | 3-methylbutyl | I | 672.0 |
| 17 | Et | 2-Pyr | 3-methylbutyl | I | 672.0 |
| 18 | Et | —N(Me)iPr | 3,3-dimethylbut-2-enyl | G | 663.9 |
| 19 | Pr | —NHiPr | n-butyl | C | 652.0 |
| 20 | Pr | —NHiPr | 3-methylbutyl | C | 666.1 |
| 21 | Pr | —N(CH$_2$CH$_2$)$_2$O | 3-methylbutyl | 3-methylbutyl | 694.5 |
| 22 | Pr | —NHiPr | 3,3-dimethylbutyl | F | 680.3 |
| 23 | Pr | —NHiPr | t-butyl | F | 652.1 |
| 24 | Pr | —N(Me)$_2$ | 3-methylbutyl | E | 652.0 |
| 25 | Bu | —N(Me)iPr | n-butyl | A = a,b,c,d,f,h | 680.5 |
| 26 | Bu | —N(Me)iPr | 2-cyclopropylethyl | A | 692.4 |
| 27 | Bu | —N(Me)iPr | 3-methylbutyl | A | 695.0 |
| 28 | Bu | —N(CH$_2$CH$_2$)$_2$NMe | 3-methylbutyl | 3-methylbutyl | 721.7 |

Preparation Of Starting Materials

EXAMPLE 1

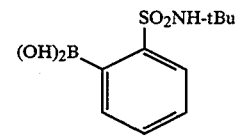

To a solution of N-t-butyl phenylsulfonamide (1 eq) in THF cooled to $-78°$ was added butyllithium solution in hexane (2.5 eq). The reaction was allowed to warm to $0°$, stirred for 1 hour and cooled to $-20°$.

Triisopropyl borate (2.5 eq) was added, the reaction was allowed to warm to room temperature and stirred for 14 hr. 2M HCl was added and after stirring for 1 hr the solvent was stripped and the product was extracted with ethyl acetate. The organic extract was washed with brine, dried over magnesium sulfate and concentrated under reduced pressure to produce the title product in form of thick syrup, which was used in further steps without further purification.

EXAMPLE 2

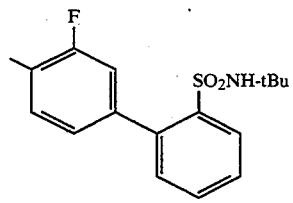

4-Bromo-2-fluorotoluene (3.46 ml, 27.5 mmol) and the product of the Example 1 (7.08 g, 27.5 mmol) were refluxed gently for 24 hr under argon in the presence of (Ph$_3$P)$_4$Pd catalyst (1.0 g) in a mixture of toluene (200 ml) ethanol(60 ml) and 1.25M aqueous NaOH (50 ml). The organic layer was separated, dried over sodium sulfate and evaporated. The oily residue was purified by flash chromatography over silica gel in methylene chloride to produce the title product.

$^1$H-NMR (CDCl$_3$): σ 1.03 (s, 9H), 2.33 (d, J=2 Hz, 3H), 3.62 (s, 1H), 7.15–7.31 (m, 4H), 7.43–7.61 (m, 2H), 8.16 (dd, J=6.0, 1.6 Hz, 1H).

EXAMPLE 3

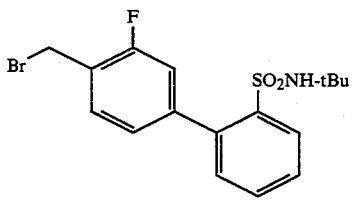

The product of the Example 2 (6.0 g, 18.7 mmol) and N-bromosuccinimide (3.35 g, 18.7 mmol) were refluxed gently for 6 hr in carbon tetrachloride in the presence of AIBN catalyst (0.15 g). After cooling the reaction to room temperature the insoluble material was filtered off and discarded. The filtrate was cooled to −20° and the crystalline title product formed was filtered off and dried.

$^1$H-NMR (CDCl$_3$): σ 1.42 (s, 9H), 3.61 (s, 1H), 4.57 (s, 2H), 7.22–7.34 (m, 3H), 7.43–7.62 (m, 3H), 8.18 (dd, J=6.0, 1.6 Hz, 1H).

EXAMPLE 4

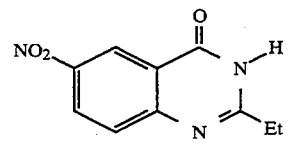

6-nitro-2-ethyl-quinazoline-4(3H)-one

To a refluxed suspension of 2-cyano-4-nitroaniline (48.9 g, 0.30 mol) in methylene chloride (600 ml) triethylamine (63 ml) and DMAP (1.83 g) were added followed by portionwise addition of propionyl chloride (31.3 ml, 0.36 mol). Reflux was continued until no starting material was present by TLC (CH$_2$Cl$_2$). The supernatant solution was decanted from the precipitate formed, concentrated to about ½ volume and the new portion of crystalline precipitate was combined with the first crop and washed with methanol to yield 51.9 g (80%) of crystalline product. The so obtained intermediate was suspended in MeOH (900 ml) and 3M NaOH solution (234 ml) was added followed by 30% hydrogen peroxide (111 ml). After refluxing for 1 hour the mixture was cooled and the precipitate formed was filtered off and discarded. To the filtrate NH$_4$Cl (43 g) in water (200 ml) was added and the yellow precipitate formed was filtered off, washed with water, dried and washed with hot ethanol. The crystalline product obtained from ethanol washings was combined with the undissolved solid $^1$H-NMR (CDCl$_3$/CD$_3$OD-2/1): σ 1.35 (t, J=7.6 Hz, 3H), 2.70 (d, J=7.6 Hz, 2H), 7.74 (d, J=9.2 Hz, 1H), 8.48 (dd, J=9.6 Hz, J=2.8 Hz, 1H), 9.01 (d, J=2.8 Hz, 1H).

EXAMPLE 5

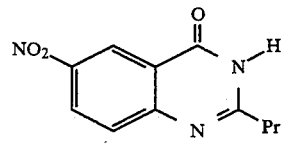

6-Nitro-2-propyl-quinazolin-4(1H)-one

To a solution of 16.3 g (0.1 mol) of 2-amino-5-nitrobenzonitrile in 200 ml of CH$_2$Cl$_2$ at 0° C. was added 21 ml (0.15 mol) of triethyl amine followed by 0.3 g of DMAP and 11.71 g (0.11 mol) of butyryl chloride. The reaction mixture was warmed to room temperature and then heated over night at 50° C. The solution was washed with 1N HCl (1×20 ml), water (1×20 ml), saturated NaHCO$_3$ (2×20 ml) and brine (1×20 ml) and dried over MgSO$_4$. The solution was filtered and concentrated in vacuo. The residue was dissolved in 200 ml of MeOH to which was added 44 ml (0.22 mol) of 5M NaOH solution followed by the dropwise addition of 25 ml (0.22 mol) 30% H$_2$O$_2$ and 50 ml of water. The mixture was refuxed for 4 hours, cooled and filtered. The filtrate was acidified with 1N HCl and the resulting precipitate recovered by filtration. The residue was recrystalized from MeOH to provide the title compound.

$^1$H-NMR (CDCl$_3$): 1.10 (t, 3H, J=7.4 Hz), 1.93 (m, 2H), 2.79 (3 line m, 2H, J=7.3 Hz), 7.80 (d, 1H, J=8.9 Hz), 8.55 (dd, 1H, J=2.5, 8.8 Hz), 9.14 (bs, 1H).

EXAMPLE 6

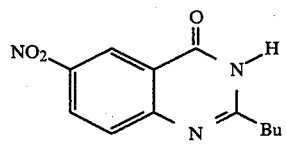

2-Butyl-6-nitro-quinazolin-4(1H)-one

The title compound was prepared as described above in Example 5 utilizing pentanoyl chloride in place of butyroyl chloride.

1H-NMR (CDCl3): 1.02 (t, 3H, J=7.32 Hz), 1.52 (m, 2H), 1.90 (m, 2H), 2.82 (dd, 2H, J=8.03 Hz), 7.82 (d, 1H, J=9.01 Hz), 8.56 (dd, 1H, J=2.6, 8.9 Hz), 9.14 (d, 1H, J=2.71 Hz).

EXAMPLE 7

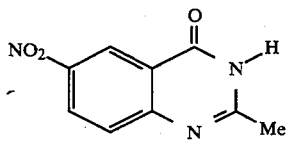

6-Nitro-2-methyl-quinazoline-4(3H)-one was prepared in a manner analogous to that described for the Example 4.

Preparations of
6-Amino-2-Alkyl-Quinazoline-4(3H)-Ones

EXAMPLE 8

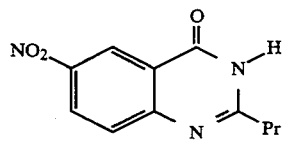

6-Amino-2-propyl-quinazoline-4(3H)-one

The quinazolinone prepared in the Example 5 (3.0 g) was dissolved in acetic acid (150 ml) on heating and the hydrogenation Was carried out under 1 atm H2 in the presence of 10% Pd on carbon catalyst (0.45 g) until no starting material was present by TLC. The reaction mixture was filtered through Celite and evaporated to produce the title product.

1H-NMR (CDCl3/CD3OD-2/1): σ 0.97 (t, J=7.4 Hz, 3H), 1.75 (m, 2H), 2.57 (t, J=7.4 Hz, 2H), 7.12 (dd, J=8.8 Hz,J=3.0 Hz, 1H), 7.33 (d, J=3.0 Hz, 1H), 7.42 (d, J=8.8 Hz, 1H).

EXAMPLE 9

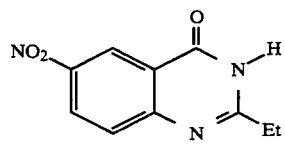

6-Amino-2-ethyl-quinazoline-4(3H)-one

The title product was obtained following the procedure analogous to that described above for Example 8.

1H-NMR (CDCl3/CD3OD-2/1): σ 1.31(t, J=7.6 Hz, 3H), 2.64 (q, J=7.6 Hz, 2H), 7.12 (dd, J=8.8, 2.6 Hz, 1H), 7.35 (d, J=2.4 Hz, 1H), 7.45 (d, J=8.8 Hz, 1H).

EXAMPLE 10

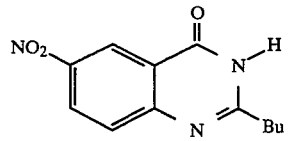

6-amino-2-butyl-quinazoline-4(3H)-one

The title product was obtained following the procedure analogous to that described above for Example 8.

Preparations Of The Compounds Of Formula 1
Tabulated In Table 1

EXAMPLE 11 (EXAMPLE OF ROUTE E, STEPS c,f,e,g.)

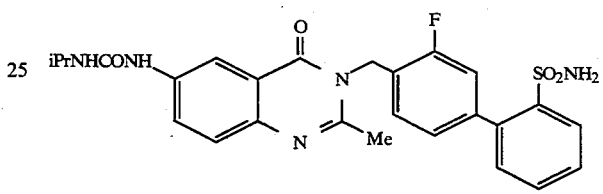

The product of Example 7 (0.8 g, 3.72 mmol) was hydrogenated under 1 atm H2 in presence of 10% Pd on carbon catalyst in dioxane (20 ml) until no starting material was present. The reaction mixture was filtered through Celite and the filter cake was washed with pyridine to dissolve the product precipitate. The combined filtrates were evaporated to dryness to produce the solid crude aminoquinazolinone. The crude material was reacted with isopropyl isocyanate (1.0 ml, 10.18 mmol, 2.73 eq) in pyridine (20 ml) overnight at room temperature and evaporated under reduced pressure. The remaining solid was reacted with the product of the Example 3 (2.23 g, 1.5 eq) in DMF (20 ml) in presence of powdered potassium carbonate (3.5 g, 6.8 eq) at room temperature overnight. Upon dilution of the reaction with water the crude mixture of N and O alkylated products precipitates as brown sold. The precipitate was filtered off, rinsed with water and dried under reduced pressure. After 14 hr deprotection in TFA (20 ml) in presence of anisole (2 ml) at room temperature ethyl acetate was added (80 ml) and the mixture was concentrated under reduced pressure. The resulting thick oil was redissolved in ethyl acetate and washed with 10% sodium bicarbonate, followed by washing with water. The title product, which precipitated from the organic phase as pale brown solid was filtered off and dried.

1H-NMR (CDCl3/CD3OD-2/1): σ 0.97 (d, J=6.6 Hz, 6H), 2.40 (s, 3H), 3.72 (sept, J=6.6 Hz, 1H), 5.26 (s, 2H), 6.86 (t, J=7.6 Hz, 1H), 6.93–7.09 (m, 3H), 7.26–7.38 (m, 4H), 7.77–7.92 (m, 3H),

EXAMPLE 12 (COMPOUND 1, TABLE 1) (EXAMPLE OF ROUTE E, STEP h.)

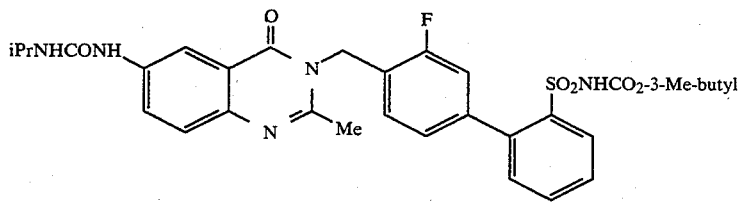

Compound 1 from Table 1

To a solution of the product of Example 11 (37 mg, 0.07 mmol) and DMAP (50 mg, 0.41 mmol) in pyridine (1.0 ml) 3-methylbutyl chloroformate (0.15 ml, 1.08 mmol) was added at room temperature and stirred for 14 hrs. The reaction was diluted with methylene chloride and washed with 0.2M HCl. Purification by radial chromatography on silica gel eluting with hexane/ethyl acetate/acetic acid-10/20/1 produced the title product.
$^1$H-NMR (CDCl$_3$/CD$_3$OD-2/1): $\sigma$ 0.74 (d, J=6.6 Hz, 6H), 1.14 (d, J=6.6 Hz, 6H), 1.22–1.44 (m, 3H), 2.60 (s, 3H), 3.82–4.00 (m, 3H), 5.42 (s, 2H), 6.89–7.16 (m, 3H), 7.24 (dd, J=7.2, 1.6 Hz, 1H), 7.49–7.65 (m, 3H), 7.95–8.01 (m, 2H), 8.17 (dd, J=6.6, 1.6 Hz, 1H).

EXAMPLE 13 (EXAMPLE OF ROUTE B, STEP f)

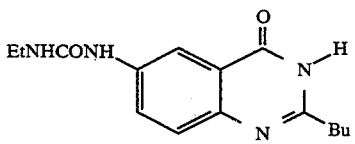

The product of Example 10 (3.86 g, 1.0 eq) was treated with ethyl isocyanate (5.0 ml, 3.5 eq) in a mixture of dioxane (60 ml) and methylene chloride (40 ml) at room temperature for 14 hr. The crystalline product formed was filtered off and washed with methylene chloride.
$^1$H-NMR (CDCl$_3$/CD$_3$OD-2/1): $\sigma$ 0.92 (t, J=7.2 Hz, 3H), 1.13 (t, J=7.2 Hz, 3H), 1.31–1.49 (m, 2H), 1.65–1.71 (m, 2H), 2.58–2.66 (m, 2H), 3.22 (q, J=7.2 Hz, 2H), 7.47–7.52 (m, 1H), 7.92–7.97 (m, 2H).

EXAMPLE 14 (EXAMPLE OF ROUTE B, STEP a)

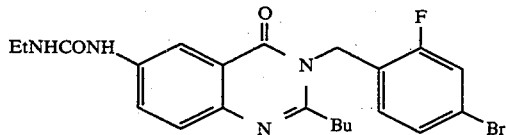

The suspension of the product of Example 13 (3.11 g, 1.0 eq) in DMF (80 ml) potassium carbonate (10.0 g, 6.6 eq) was sonicated and warmed to 50° until the starting material dissolved. To the yellow solution 4-bromo-2-fluoro benzyl bromide (3.23 g, 1.1 eq) was added and the reaction was stirred for 14 hrs at room temperature Dilution with water precipitated the mixture of products, which was filtered off, washed with water and dried. Recrystallization from ethyl acetate yielded pure crystalline N-alkylation product while the O-alkylation byproduct remained in mother liquors.
$^1$H-NMR (CDCl$_3$/CD$_3$OD-2/1): $\sigma$ 0.88 (t, J=7.2 Hz, 3H), 1.13 (t, J=7.2 Hz, 3H), 1.30–1.48 (m, 2H), 1.60–1.78 (m, 2H), 2.64–2.72 (m, 2H), 3.22 (q, J=7.2 Hz, 2H), 5.33 (s, 2H), 6.82 (t, J=8.0 Hz, 1H), 7.15–7.21 (m, 1H), 7.28 (dd, J=9.6, 1.8 Hz, 1H), 7.56 (d, J=9.0 Hz, 1H), 7.92 (d, J=2.4 Hz, 1H), 8.05 (dd, J=9.0, 2.6 Hz, 1H).

EXAMPLE 15 (EXAMPLE OF ROUTE B, STEPS b,d)

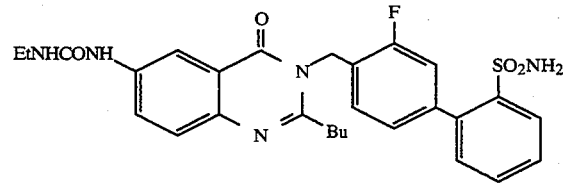

A mixture of the product of Example 14 (3.18 g, 6.7 mmol) and the boronic acid of Example 1 (3.44, 13.4 mmol) was gently refluxed (100° oil bath) in toluene(100 ml)/ethanol (25 ml)/1.25M aqueous NaOH (25 ml) under argon in the presence of (Ph$_3$P)$_4$Pd catalyst (0.5 g) for 14 hrs. The reaction was diluted with ethyl acetate and washed with water and dil. HCl. The organic layer was dried and concentrated under reduced pressure to produce the solid intermediate, which was deprotected by treatment with TFA (50 ml) in the presence of anisole (3.0 ml) at room temperature for 14 hrs. After the workup of the deprotection reaction analogous to that of Example 11 the crystalline title product was obtained.
$^1$H-NMR (CDCl$_3$/CD$_3$OD-2/1): $\sigma$ 83A115/83a 0.88 (t, J=7.2 Hz, 3H), 1.13 (t, J=7.2 Hz, 3H), 1.30–1.48 (m, 2H), 1.60–1.78 (m, 2H), 2.64–2.72 (m, 2H), 3.22 (q, J=7.2 Hz, 2H), 5.44 (s, 2H), 6.94 (t, J=7.8 Hz, 1H), 7.12 (dd, J=7.8, 1.6 Hz, 1H), 7.20–7.26 (m, 2H), 7.42–7.60 (m, 4H), 7.95 (d, J=2.2 Hz, 1H), 8.01–8.09 (m, 2H).

EXAMPLE 16 (EXAMPLE OF ROUTE B, STEP g)

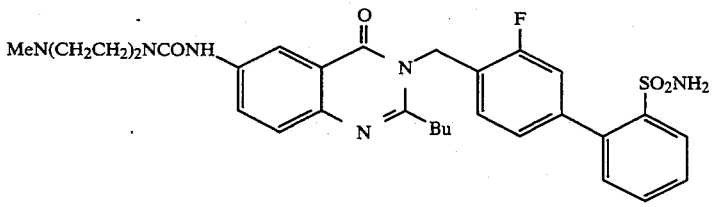

The solution product of Example 15 (131 mg) in N—Me piperazine (3.0 ml) was heated at 140° in pressure robe for 2 hr. After removing the excess amine under reduced pressure the pure title product was obtained by radial chromatography over silica gel eluting with methylene chloride/methanol-10/1.

$^1$H-NMR (CDCl$_3$/CD$_3$OD-2/1): σ 111A116/111a 0.91 (t, J=7.0 Hz, 3H), 1.32–1.51 (m, 2H), 1.65–1.81 (m, 2H), 2.32 (s, 3H), 2.48 (m, 4H), 3.56 (m, 4H), 5.44 (s, 2H), 6.94 (t, J=7.8 Hz, 1H), 7.06–7.26 (m, 3H), 7.43–7.61 (m, 4H), 7.96–8.08 (m, 3H).

EXAMPLE 17 (COMPOUND 28, TABLE 1) (EXAMPLE OF ROUTE B, STEP h)

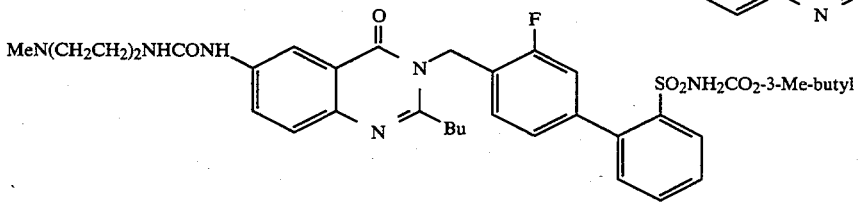

Compound 28 Table 1

To a solution of the product of Example 16 (49 mg, 0.076 mmol) and DMAP(39 mg, 0.32 mmol) in pyridine (1.0 ml) 3-methylbutyl chloroformate (0.1 ml, 0.72 mmol) was added at room temperature and stirred for 14 hrs. The reaction was diluted with methylene chloride and washed with 0.2M HCl. Purification by radial chromatography over silica gel eluting with methylene chloride/methanol-10/1 gave the title product.

$^1$H-NMR (CDCl$_3$/CD$_3$OD-2/1): σ 0.76 (d, J=6.2 Hz, 6H), 0.89 (t, J=7.2 Hz, 3H), 1.21–1.50 (m, 5H), 1.66–1.81 (m, 2H), 2.62 (s, 3H), 2.74 (t, J=7.2 Hz, 2H), 2.97 (br.s, 4H), 3.62 (br.s, 4H), 5.39 (br.s, 2H), 6.83 (t, J=7.8 Hz, 1H), 7.03–7.17 (m, 3H), 7.42 (s, 1H), 7.48–7.55 (m, 2H), 7.64 (d, J=9.2 Hz, 1H), 8.15–8.28 (m, 3H).

EXAMPLE 18 (EXAMPLE OF ROUTE A, STEP a)

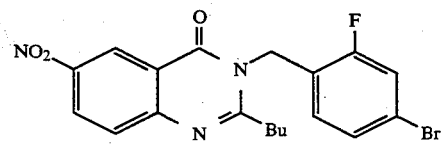

The product of Example 6 (2.81 g, 11.4 mmol) was alkylated with 4-bromo-2-fluoro benzyl bromide (3.05 g, 11.4 mmol) in DMF (50 ml) in the presence of potassium carbonate (10 g, 72.5 mmol) at room temp for 14 hr. The reaction was diluted with water and the product was extracted with ethyl acetate and the organic layer was washed with dil. HCl and brine. Evaporation of solvent under reduced pressure furnished the solid, which was recrystallized from ethyl acetate/hexane-1/1 to produce the pale yellow crystalline title product.

$^1$H-NMR (CDCl$_3$): σ 0.94 (t, J=7.2 Hz, 3H), 1.33–1.52 (m, 2H), 1.70–1.87 (m, 2H), 2.73–2.80 (m, 2H), 6.95 (t, J=7.8 Hz, 1H), 7.20–7.34 (m, 2H), 7.77 (d, J=8.8 Hz, 1H), 8.53 (dd, J=9.0, 2.6 Hz, 1H), 9.15 (d, J=2.0 Hz, 1H).

EXAMPLE 19 (EXAMPLE OF ROUTE A, STEPS b,d)

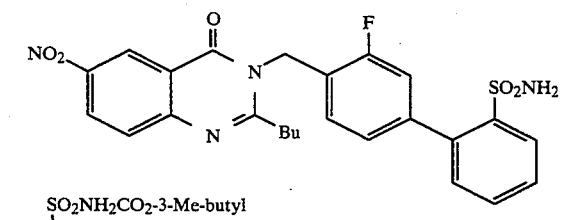

A mixture of the product of Example 18 (1.44 g, 33.3 mmol)and the boronic acid of Example 1 (1.28 g, 5.0 mmol) was gently refluxed (100° oil bath) in toluene(30 ml)/ethanol(20 ml)/1.25M aqueous NaOH (10 ml) under argon in presence of (Ph$_3$P)$_4$Pd catalyst (0.3 g) for 14 hrs. The reaction was diluted with ethyl acetate, the organic was washed with 1.25M aqueous NaOH, water and dilute HCl. The organic layer was dried and concentrated under reduced pressure to produce the oily intermediate, which was deprotected by treatment with TFA (50 ml) in presence of anisole (1.0 ml) at room temperature for 14 hrs. After the workup of the deprotection reaction analogous to that of Example 11 the title product was obtained by radial chromatography over silica gel plate during with methylene chloride/methanol-40/1.

EXAMPLE 20 (EXAMPLE OF ROUTE A, STEP c)

EXAMPLE 22 (COMPOUND 25, TABLE 1) (EXAMPLE OF ROUTE A, STEP h)

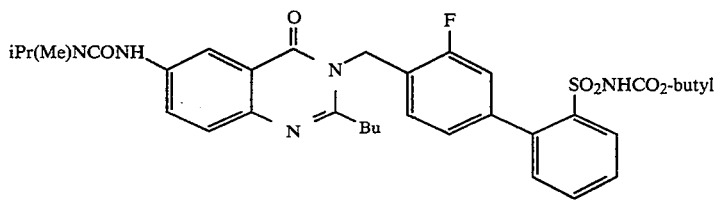

Compound 25 Table 1

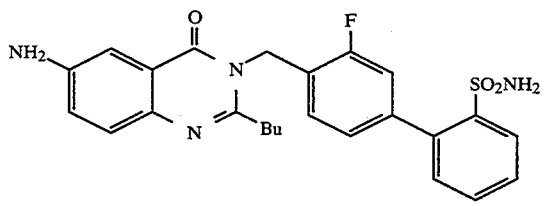

The product of Example 19 (0.65 g) was hydrogenated under 1 atm $H_2$ in ethanol (20 ml) in the presence of 10% Pd on carbon catalyst until no starting material was present by TLC. After filtration through Celite the solvent was removed under reduced pressure and the residue was purified by radial chromatography over silica gel eluting with methylene chloride/methanol-20/1 to produce the title compound.

$^1$H-NMR (CDCl$_3$/CD$_3$OD-2/1): σ 0.90 (t, J=7.2 Hz, 3H), 1.32–1.50 (m, 2H), 1.62–1.78 (m, 2H), 2.70–2.78 (m, 2H), 5.43 (s, 2H), 6.93 (t, J=7.8 Hz, 1H), 7.09–7.26 (m, 4H), 7.35–7.49 (m, 4H), 8.07 (dd, J=7.8, 1.6 Hz, 1H).

EXAMPLE 21 (EXAMPLE OF ROUTE A, STEP f)

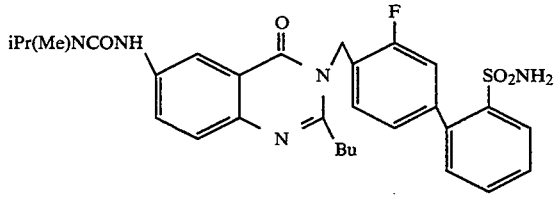

To the solution of the product of Example 20 (167 mg., 0.35 mmol) in methylene chloride (3.0 ml) in the presence of powdered potassium carbonate (480 mg, 3.5 mmol) a solution of triphosgene (35 mg, 0.12 mmol) in methylene chloride (0.5 ml) was added at room temperature After 30 min. N-methyl-i-propylamine (0.18 ml, 3.5 mmol) was added and the reaction was stirred at room temp for 1.4 hr. The mixture was filtered and the filtrate was concentrated under reduced pressure. The residue was purified by radial chromatography over silica gel plate eluting with methylene chloride/methanol-20/1 to produce the title compound.

$^1$H-NMR (CDCl$_3$/CD$_3$OD-2/1): σ 0.91 (t, J=7.4 Hz, 3H), 1.14 (d, J=6.6 Hz, 6H), 1.33–1.51 (m, 2H), 1.65–1.80 (m, 2H), 1.74–2.85 (m, 5H), 4.51 (sept, J=6.6 Hz, 1H), 5.44 (s, 2H), 6.95 (t, J=8.0 Hz, 1H), 7.12 (br.d, J=8.0 Hz, 2H), 7.20–7.25 (m, 1H), 7.42–7.61 (m, 3H), 8.00–8.08 (m, 3H).

To the solution of the product of Example 21 (55 mg, 0.095 mmol) and DMAP (25 mg, 0.20 mmol) in pyridine (1.0 ml) butyl chloroformate (0.1 ml, 0.79 mmol) was added at room temperature and stirred for 2 hrs. The reaction was diluted with methylene chloride and washed with 0.2M HCl. Purification by radial chromatography over silica gel eluting with methylene chloride/methanol-20/1 gave the title product.

$^1$H-NMR (CDCl$_3$/CD$_3$OD-2/1): σ 0.79 (t, J=7.2 Hz, 3H), 0.96 (t, J=7.4 Hz, 3H), 1.14 (d, J=6.8 Hz, 6H), 1.30–1.51 (m, 4H), 1.68–1.84 (m, 2H), 2.76–2.85 (m, 5H), 3.90 (t, J=6.6 Hz, 2H), 4.51 (sept, J=6.8 Hz, 1H), 5.43 (s, 1H), 6.92 (t, J=7.6 Hz, 1H), 7.03 (dd, J=9.2, 1.4 Hz, 1H), 7.09 (dd, J=10.8, 1.4 Hz, 1H), 7.48–7.64 (m, 3H), 7.98–8.03 (m, 2H), 8.17 (dd, J=7.6, 1.6 Hz, 1H).

EXAMPLE 23 (EXAMPLE OF ROUTE H, STEPS e,d)

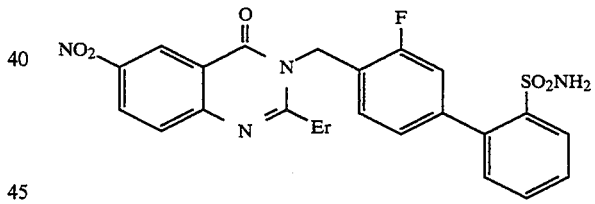

To a suspension of the products of Example 4 (1.12 g, 5.15 mmol) and Example 3 (2.07 g, 4.91 mmol) in DMF (40 ml) powdered potassium carbonate (2.03 g, 14.73 mmol) was added. After 14 hr stirring at room temperature the product was precipitated by addition of water (200 ml). The precipitate was filtered off, washed with water, dissolved in methylene chloride and dried. The solvent was evaporated and the residue was purified by flash chromatography with methylene chloride/methanol-100/1. The fraction containing the inseparable mixture of N and O alkylated products was treated with TFA (15 ml) in the presence of anisole (0.5 ml) at room temperature for 14 hrs. After the workup of the TFA deprotection reaction analogous to that of Example 11 the title product was purified by radial chromatography over silica gel eluting with methylene chloride/methanol-20/1 to produce the title compound.

$^1$H-NMR (CDCl$_3$/CD$_3$OD-2/1): σ 1.37 (t, J=7.2 Hz, 3H), 2.91 (q, J=7.2 Hz, 2H), 5.49 (s, 2H), 7.07 (t, J=7.6 Hz, 1H), 7.13–7.27 (m, 3H), 7.43–7.55 (m, 2H), 7.81 (d, J=9.0 Hz, 1H), 8.06 (dd, J=7.2, 2.2 Hz, 1H), 8.52 (dd, J=7.2, 2.4 Hz, 1H), 9.07 (d, J=2.6 Hz, 1H).

EXAMPLE 24 (EXAMPLE OF ROUTE H, STEP c)

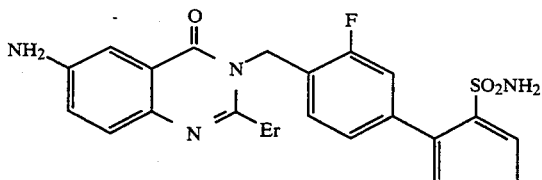

Compound 6 Table 1

The product of the Example 23 (9.5 g) was hydrogenated in acetic acid solution under 1 atm. of H₂ in presence of 10% Pd on carbon catalyst at room temperature for 14 hrs. The reaction was filtered through Celite, concentrated under reduced pressure and the solid residue was evaporated to dryness several times following redissolution in ethyl acetate to remove remaining the acetic acid by azeotrozic distillation.

EXAMPLE 25 (EXAMPLE OF ROUTE H. STEP f)

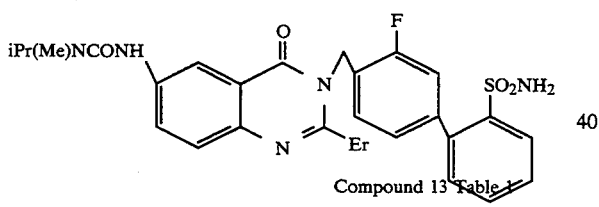

Compound 13 Table 1

To the solution of the product of Example 24 (5.04g, 11.15 mmol) in ethyl acetate (150 ml) cooled to 0° was added a solution of phosgene in toluene (1.93M, 9.7 ml, 18.7 mmol). The resulting suspension of fine precipitate was Stirred at room temp for 2 hr and N-methyl-i-propylamine (5.0 ml, 47.9 mmol) was added in one portion, upon which most of the precipitate dissolved. To dissolve some of the gummy product formed THF (100 ml) was added and the reaction mixture was heated to 60°. After concentrating the reaction under reduced pressure ethyl acetate was added to the oily residue. The title product, which slowly crystallized from ethyl acetate solution was filtered and washed with ethyl acetate.

¹H-NMR (CDCl₃/CD₃OD-2/1): σ 1.15 (d, J=6.2 Hz, 6H), 1.34 (t, J=7.2 Hz, 2H), 2.75-2.85 (m, 5H), 4.51 (sept, J=6.6 Hz, 1H), 5.46 (s, 2H), 6.97 (t, J=7.4 Hz, 1H), 7.12 (d, J=8.4 Hz, 1H), 7.20-7.26 (m, 2H), 7.46-7.63 (m, 4H), 8.00-8.09 (m, 3H).

EXAMPLE 26 (COMPOUND 6, TABLE 1)
EXAMPLE OF ROUTE H, STEP h)

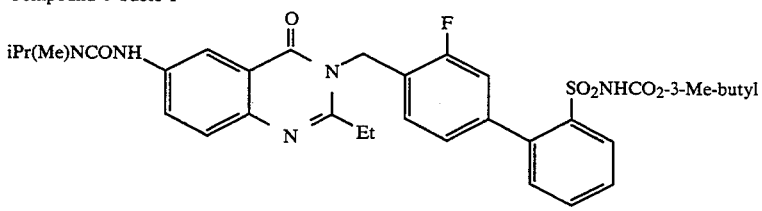

The product of the Example 25 (0.776 g, 1.41 mmol) dissolved in pyridine (15 ml) in the presence of DMAP (0.74 g, 6.06 mmol) was treated portionwise with 3-methyl-butyl chloroformate (2.4 ml., 17.0 mmol) at room temperature. After 16 hr the reaction was diluted with methylene chloride/ethyl acetate and washed with 0.5M aqueous citric acid solution. The organic layer was separated, dried and the title product was isolated by radial chromatography over silica gel eluting with hexane/ethyl acetate/acetic acid-10/10/1.

¹H-NMR (CDCl₃/CD₃OD-2/1): σ 0.75 (d, J=6.2 Hz, 6H), 1.15 (d, J=6.6 Hz, 6H), 1.27-1.40 (m, 6H), 2.80-2.92 (m, 5H), 3.94 (d, J=6.4 Hz, 2H), 4.51 (sept, J=6.6 Hz, 1H), 5.45 (s, 2H), 6.87 (t, J=7.8 Hz, 1H), 7.00 (dd, J=8.0, 1.6 Hz, 1H), 7.10 (dd, J=10.8, 1.4 Hz, 1H), 7.25 (dd, J=7.6, 1.6 Hz, 1H), 7.50-7.65 (m, 3H), 7.98-8.06 (m, 2H), 8.17 (dd, J=7.8, 1.6 Hz, H).

EXAMPLE 27 (COMPOUND 13, TABLE 1)
(EXAMPLE OF ROUTE H, STEP h)

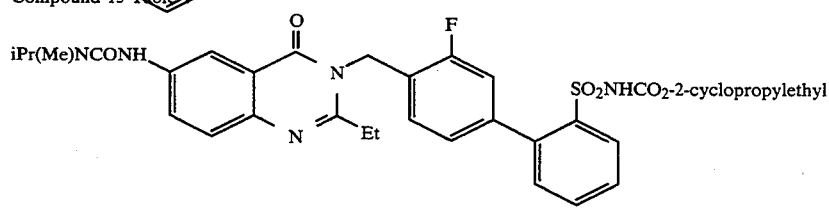

The product of the Example 25 (0.579 g, 1.05 mmol) dissolved in pyridine (5 ml) in the presence of DMAP (0.36 g, 2.95 mmol) was treated portionwise with 2-cyclopropylethyl chloroformate (0.6 ml., 4.3 mmol) at room temperature After 16 hr the reaction was diluted with methylene chloride and washed with 0.2M HCl. The organic layer was separated, dried and the title product was isolated by radial chromatography over silica gel eluting with hexane/ethyl acetate/acetic acid-10/10/1. The eluate was evaporated following addition of toluene to remove the residual acetic acid by azeotropic distillation and the title product was crystallized from toluene.

¹H-NMR (CDCl₃/CD₃OD-2/1): σ 0.11-0.08 (m, 2H), 0.22-0.31 (m, 2H), 0.35-0.50 (m, 1H), 1.15 (d, J=6.6 Hz, 6H), 1.27-1.39 (m, 5H), 2.78-2.87 (m, 5H), 3.96 (t, J=6.6 Hz, 2H), 4.51 (sept, J=6.6 Hz, 1H), 5.43

(s, 2H), 6.85 (t, J=7.8 Hz, 1H), 6.98-7.27 (m, 4H), 7.52-7.64 (m, 3H), 8.00-8.03 (m, 2H), 8.18 (dd, J=7.6, 1.6 Hz, 1H).

EXAMPLE 28 (EXAMPLE OF ROUTE H, STEP j)

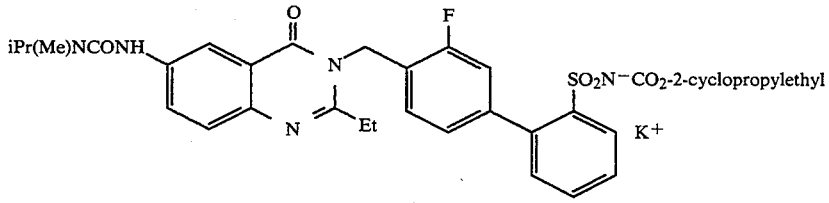

The product of the Example 27 (0.40 g) was converted into its potassium salt by addition of methanol (1.0 ml) and methanolic potassium hydroxide solution (0.504M, 1.29 ml, 1.05 eq) followed by the slow addition of diethyl ether (4.0 ml). After 14 hr stirring the resulting crystalline potassium salt was filtered and dried under reduced pressure.

EXAMPLE 29 (EXAMPLE OF ROUTE C STEP f)

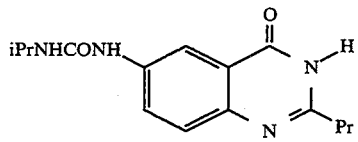

The product of the Example 8 (0.76 g, 3.74 mmol) was reacted with isopropyl isocyanate (0.76 ml, 8.94 mmol) in DMF at room temperature for 14 hr. The reaction mixture was diluted with water and the precipitate of the title product formed was filtered and dried.

$^1$H-NMR (CDCl$_3$/CD$_3$OD-2/1): σ 0.98 (t, J=7.4 Hz, 3H), 1.14 (d, J=6.6 Hz, 6H), 1.70-1.88 (m, 2H), 2.59 (t, J=7.8 Hz, 2H), 3.78 (s, 1H), 7.52 (d, J=9.0 Hz, 1H), 7.89 (d, J=2.4 Hz, 1H), 7.99 (dd, J=8.8, 2.8 Hz, 1H).

EXAMPLE 30 (EXAMPLE OF ROUTE C STEP a)

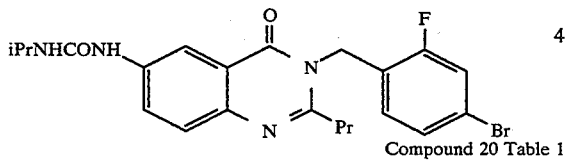
Compound 20 Table 1

The product of the Example 29 (177 mg, 0.61 mmol) was reacted with 4-bromo-2-fluorobenzyl bromide (0.163 g, 0.61 mmol) in the presence of powdered potassium carbonate (1.0 g, 7.24 mmol) in DMF (5.0 ml). The reaction mixture was diluted with water and extracted with ethyl acetate. The organic layer was separated, dried and evaporated and the residue was purified by radial chromatography over silica gel eluting with methylene chloride/methanol-20/1 to furnish the title product.

$^1$H-NMR (CDCl$_3$/CD$_3$OD-2/1): σ 0.97 (t, J=7.4 Hz, 3H), 1.14 (d, J=6.6 Hz, 6H), 1.63-1.82 (m, 2H), 2.65 (t, J=8.0 Hz, 2H), 3.88 (sept, J=6.6 Hz, 1H), 5.32 (s, 2H), 6.81 (t, J=8.2 Hz, 1H), 7.17 (dd, J=8.0, 1.4 Hz, 1H), 7.27 (dd, J=9.8, 2.0 Hz, 1H), 7.55 (d, J=8.8 Hz, 1H), 7.89 (d, J=2.4 Hz, 1H), 8.04 (dd, J=8.8, 2.6 Hz, 1H).

EXAMPLE 31 (EXAMPLE OF ROUTE C, STEPS b,d)

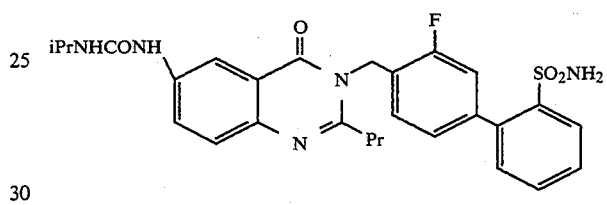

The product of the Example 30 (57 mg, 0.12 mmol) was reacted with the product of the Example 1 (150 mg, 0.58 mmol) in the presence of (Ph$_3$P)$_4$Pd catalyst (15 mg) for 14 hrs. After the workup analogous to that of the Example 15 the title product was isolated by radial chromatography over silica gel eluting with methylene chloride/methanol-20/1.

$^1$H-NMR (CDCl$_3$/CD$_3$OD-2/1): σ 1.01 (t, J=7.4 Hz, 3H), 1.14 (d, J=6.6 Hz, 6H), 1.68-1.88 (m, 2H), 2.75 (t, J=7.8 Hz, 2H), 3.88 (sept, J=6.6 Hz, 1H), 5.43 (s, 2H), 6.98 (t, J=7.8 Hz, 1H), 7.11 (dd, J=8.0, 1.6 Hz, 1H), 7.21 (dd, J=4.0, 1.6 Hz, 1H), 7.25 (d, J=1.6 Hz, 1H), 7.42-7.59 (m, 3H), 7.93 (d, J=2.4 Hz, 1H), 8.01-8.09 (m, 2H).

EXAMPLE 32 (COMPOUND 20, TABLE 1) (EXAMPLE OF ROUTE C, STEP h)

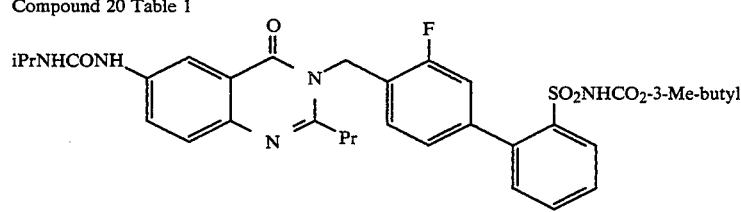

The product of the Example 31 dissolved in pyridine in the presence of DMAP was reacted with 3-Me-butyl chloroformate in a manner analogous to that of the Example 12 and the title product was isolated by radial chromatography over silica gel eluting with methylene chloride/methanol-20/1.

$^1$H-NMR (CDCl$_3$/CD$_3$OD-2/1): σ 0.74 (d, J=6.2 Hz, 6H), 1.03 (t, J=7.4 Hz, 3H), 1.14 (d, J=6.6 Hz, 6H), 1.20-1.45 (m, 3H), 1.74-1.90 (m, 1H), 2.75-2.83 (m, 2H), 3.81–3.96 (m, 3H), 5.42 (s, 2H), 6.87 (t, J=7.8 Hz, 1H), 7.00 (dd, J=8.0, 1.6 Hz, 1H), 7.08 (dd, J=10.8, 1.6 Hz, 1H), 7.27 (dd, J=7.8, 1.6 Hz, 1H), 7.50–7.66 (m, 3H), 7.98–8.04 (m, 2H), 8.17 (dd, J=7.8, 1.6 Hz, 1H).

EXAMPLE 33 (COMPOUND 4, TABLE 1) (EXAMPLE OF ROUTE D, STEPS c,f,a,b,d,h)

Compound 4 Table 1

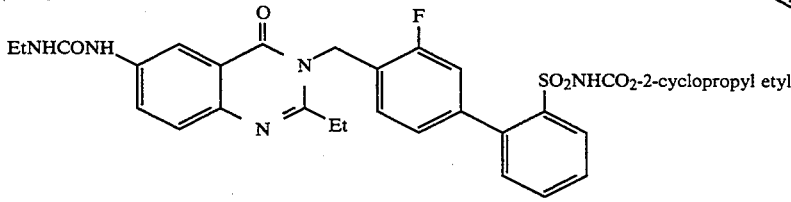

The product of Example 33 was prepared analogously to the product of Example 32 in a sequence of steps c,f,a,b,d,h.

¹H-NMR (CDCl₃/CD₃OD-2/1): σ 0.14–0.09 (m, 2H), 0.24–0.32 (m, 2H), 1.14 (t, J=7.2 Hz, 3H), 1.21–1.40 (m, 5H), 2.85 (q, J=7.4 Hz, 2H), 3.22 (q, J=7.2 Hz, 2H), 3.96 (t, J=6.6 Hz, 2H), 5.43 (s, 2H), 6.85 (t, J=7.8 Hz, 1H), 7.00 (dd, J=8.0, 1.6 Hz, 1H), 7.09 (dd, J=10.8, 1.6 Hz, 1H), 7.24 (dd, J=8.0, 1.6 Hz, 1H), 7.50–7.65 (m, 3H), 7.99–8.04 (m, 2H), 8.18 (dd, J=8.0, 1.6 Hz, 1H).

EXAMPLE 34 (COMPOUND 5, TABLE 1) (EXAMPLE OF ROUTE D, STEP i)

Compound 5 Table 1

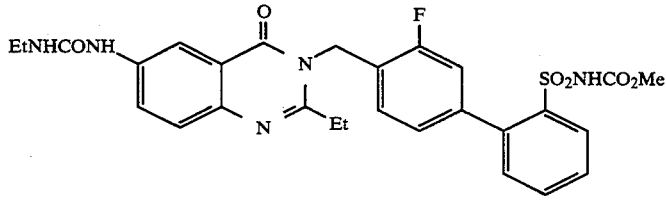

The product of Example 33 (16 mg) was heated in the pressure robe in methanol (1 ml) at 100° for 45 min. The solvent was evaporated under reduced pressure and the title product was isolated by radial chromatography over silica gel plate eluting with methylene chloride/methanol-20/1.

¹H-NMR (CDCl3/CD3OD-2/1): σ 1.13 (t, J=7.2 Hz, 3H), 1.35 (t, J=7.4 Hz, 3H), 2.85 (q, J=7.4 Hz, 2H), 3.22 (q, J=7.2 Hz, 2H), 3.52 (s, 3H), 5.44 (s, 2H), 6.88 (t, J=7.8 Hz, 1H), 6.99 (dd, J=8.0, 1.6 Hz, 1H), 7.09 (dd, J=11.0, 1.6 Hz, 1H), 7.25 (dd, J=7.4, 1,6 Hz, 1H), 7.50–7.65 (m, 3H), 7.98–8.03 (m, 2H), 8.17 (dd, J=7.6, 1.6 Hz, 1H).

EXAMPLE 35 (EXAMPLE OF ROUTE F, STEPS e,h)

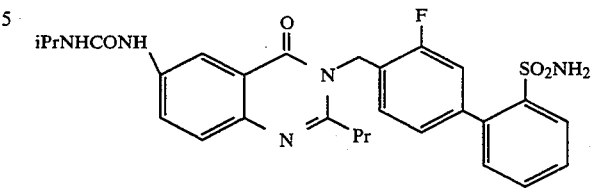

To the suspension of the product of Example 29 (0.22 g, 0.82 mmol) in DMF (10 ml) lithium hexamethyldisilazane (1.0M in THF, 0.9 ml, 0.9 mmol) was added at room temperature and after few minutes the solution of the product of Example 3 (0.36 g, 0.90 mmol) was added. After 2 hr at room temperature the reaction was diluted with water and extracted with ethyl acetate. The solvent was removed under reduced pressure and the residue was deprotected in TFA in a manner analogous to that of Example 11 yielding the product identical to that of Example 31.

EXAMPLE 36 (EXAMPLE OF ROUTE E, STEP h)

Compound 22 Table 1

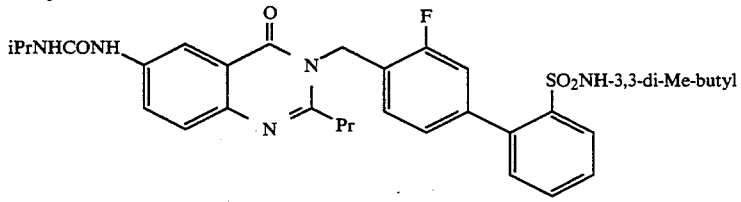

The product of Example 35 dissolved in pyridine in the presence of DMAP was reacted with 3,3-di-methyl-butyl chloroformate in a manner analogous to that of Example 12 and the title product was isolated by radial chromatography over silica gel eluting with hexane/ethylacetate/acetic acid-20/20/1.

¹H-NMR (CDCl₃/CD₃OD-2/1): σ 0.76 (s, 9H), 1.04 (t, J=7.2 Hz, 3H), 1.14 (d, J=6.6 Hz, 6H), 1.31 (t, J=7.6 Hz, 2H), 1.72–1.91 (m, 1H), 2.56–2.65 (m, 2H), 3.82–4.00 (m, 3H), 5.42 (s, 2H), 6.87 (t, J=7.8 Hz, 1H), 7.00 (dd, J=8.0, 1.6 Hz, 1H), 7.06-7.28 (m, 3H), 7.50-7.65 (m, 3H), 7.97-8.04 (m, 2H), 8.17 (dd, J=8.0, 1.6 Hz, 1H).

EXAMPLE 37 (EXAMPLE OF ROUTE G STEP f)

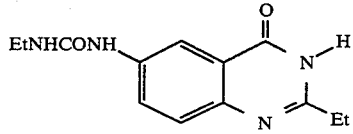

The product of the Example 9 (0.8 g, 4.17 mmol) was reacted with ethyl isocyanate (0.4 ml, 5.06 mmol) in pyridine (10 ml) at room temperature The abundant crystalline product forms after a few minutes. After 14 hrs at room temperature the reaction was diluted with ethyl acetate and the crystalline product was filtered off and dried.

$^1$H-NMR (CDCl$_3$/CD$_3$OD-2/1): σ 1.12 (t, J=7.2 Hz, 3H), 1.32 (t, J=7.6 Hz, 3H), 2.64 (q, J=7.6 Hz, 2H), 3.25 (q, J=7.2 Hz, 2H), 7.53 (d, J=8.8 Hz, 1H), 7.91 (d, J=2.4 Hz, 1H), 8.00 (dd, J=8.8, 2.4 Hz, 1H).

EXAMPLE 38 (EXAMPLE OF ROUTE G STEP a)

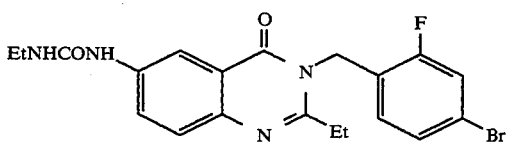

The product of the Example 37 (0.7 g, 2.7 mmol) was reacted with 4-bromo-2-fluorobenzyl bromide (0.8 g, 3.0 mmol) in the presence of powdered potassium carbonate (2.3 g, 16.7 mmol) in DMF (22.0 ml) at room temperature for 6 hrs. The reaction mixture was diluted with water and the precipitate was filtered off and washed with acetone to produce the title product.

$^1$H-NMR (CDCl$_3$/CD$_3$OD-2/1): σ 1.13 (t, J=7.2 Hz, 3H), 1.28 (t, J=7.4 Hz, 3H), 2.72 (q, J=7.6 Hz, 2H), 3.25 (q, J=7.2 Hz, 2H), 5.34 (s, 2H), 6.80 (t, J=7.8 Hz, 1H), 7.17 (dd, J=8.0, 1.6 Hz, 1H), 7.27 (dd, J=7.6, 1.8 Hz, 1H), 7.57 (d, J=9.0 Hz, 1H), 7.91 (d, J=2.4 Hz, 1H), 8.06 (dd, J=8.8, 2.6 Hz, 1H).

EXAMPLE 39 (EXAMPLE OF ROUTE G, STEPS b,d)

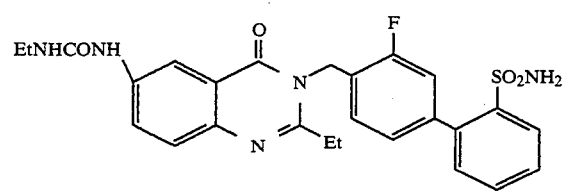

The product of Example 38 was reacted with the product of the Example 1 in a manner analogous to Example 15 and then deprotected in TFA in a manner analogous to that of the Example 11 yielding the title product.

$^1$H-NMR (CDCl$_3$/CD$_3$OD-2/1): σ 1.13 (t, J=7.2 Hz, 3H), 1.33 (t, J=7.2 Hz, 3H), 2.82 (q, J=7.4 Hz, 2H), 3.21 (q, J=7.2 Hz, 2H), 5.44 (s, 2H), 6.92 (t, J=7.8 Hz, 1H), 7.11 (dd, J=7.8, 1.6 Hz, 1H), 7.19-7.28 (m, 2H), 7.45-7.53 (m, 2H), 7.60 (d, J=9.0 Hz, 1H), 7.93 (d, J=2.4 Hz, 1H), 8.06 (dd, J=8.8, 2.4 Hz, 1H).

EXAMPLE 40 (EXAMPLE OF ROUTE G, STEPS g,h)

Compound 7 Table 1

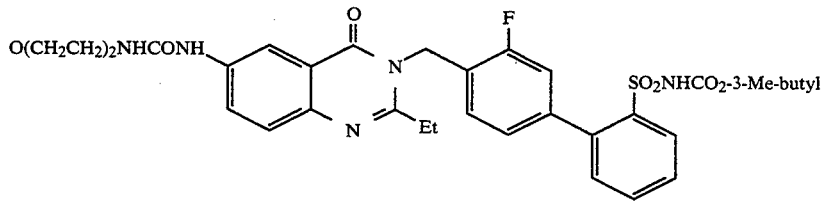

The product of Example 39 (89 mg) was reacted with morpholine (1 ml) for 2 hr at 140° C. in a pressure robe. The excess amine was removed under reduced pressure and the corresponding morpholine urea was isolated by radial chromatography over silica gel eluting with methylene chloride/methanol-20/1. The reaction of this intermediate (37 mg, 0.065 mmol) with 3-Me-butyl chloroformate (0.08 ml, 0.57 mmol) in the presence of DMAP (27 mg, 0.22 mmol) in pyridine (1 ml) for 2 hr at room temperature provided, after the standard workup and purification by radial chromatography over silica gel eluting with methylene chloride/methanol-20/1, the title product.

$^1$H-NMR (CDCl$_3$/CD$_3$OD-2/1): σ 0.74 (d, J=6.2 Hz, 6H), 1.22-1.45 (m, 5H), 2.84 (q, J=7.4 Hz, 2H), 3.49-3.54 (m, 4H), 3.68-3.73 (m, 4H), 3.93 (t, J=6.6 Hz, 2H), 5.43 (s, 2H), 6.90 (t, J=7.8 Hz, 1H), 7.00 (dd, J=9.4, 1.6 Hz, 1H), 7.09 (dd, J=10.8, 1.6 Hz, 1H), 7.25 (dd, J=7.6, 1.6 Hz, 1H), 7.50-7.65 (m, 3H), 7.96-8.03 (m, 2H), 8.17 (dd, J=7.8, 1.6 Hz, 1H).

EXAMPLE 41 (COMPOUND 8, TABLE 1) (EXAMPLE OF ROUTE G, STEP i)

Compound 8 Table 1

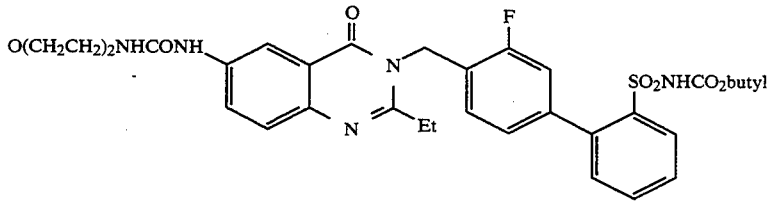

The product of Example 40 (6 mg) was heated at 110°–120° in n-butanol for 30 min. The excess alcohol was removed under reduced pressure and the title product was isolated by radial chromatography over silica gel eluting with methylene chloride/methanol-20/1.

$^1$H-NMR (CDCl$_3$/CD$_3$OD-2/1): σ 0.77 (t, J=7.2 Hz, 3H), 1.05–1.22 (m, 2H), 1.32–1.42 (m, 5H), 2.93 (q, J=7.4 Hz, 2H), 3.48–3.55 (m, 4H), 3.69–3.74 (m, 4H), 3.91 (t, J=6.6 Hz, 2H), 5.46 (s, 2H), 6.90–7.12 (m, 3H), 7.25 (dd, J=7.2, 1.6 Hz, 1H), 7.50–7.65 (m, 2H), 7.68 (d, J=9.0 Hz, 1H), 8.02 (dd, J=8.8, 2.6 Hz, 1H), 8.11–8.19 (m, 2H).

EXAMPLE 42 (EXAMPLE OF ROUTE I, STEPS h,c)

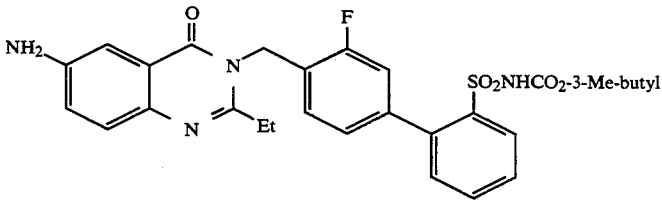

To the solution of the product of Example 23 (2.11 g, 4.37 mmol) and DMAP (1.66 g, 13.61 mmol) in pyridine (20 ml) cooled to 0° 3-Me-butyl chloroformate (2.0 ml, 14.2 mmol) was added portionwise. After 14 hr the reaction was diluted with methylene chloride and washed with 0.2M HCl. The organic layer was evaporated and the solid residue was triturated with methylene chloride/hexane-1/5 mixture. The resulting yellow solid of the intermediate sulfonylcarbamate was filtered, dried and suspended in acetic acid (100 ml). 10% Pd on carbon catalyst (0.2 g) was added and the hydrogenation was carded out at 1 atm of H$_2$. Methylene chloride (100 ml) was added, and the mixture was filtered through Celite. After concentrating to about 50 ml, toluene was added and the crystalline title product formed was filtered off and washed with toluene.

$^1$H-NMR (CDCl$_3$/CD$_3$OD-2/1): σ 0.74 (d, J=6.4 Hz, 6H), 1.22–1.42 (m, 5H), 2.83 (q, J=7.4 Hz, 2H), 3.93 (t, J=6.8 Hz, 2H), 5.42 (s, 2H), 6.88 (t, J=7.6 Hz, 1H), 6.99 (dd, J=7.8, 1.6 Hz, 1H), 7.06–7.27 (m, 4H), 7.49–7.62 (m, 3H), 8.17 (dd, J=8.0, 1.6 Hz, 1H).

EXAMPLE 43 (COMPOUND 16, TABLE 1) (EXAMPLE OF ROUTE I, STEP f)

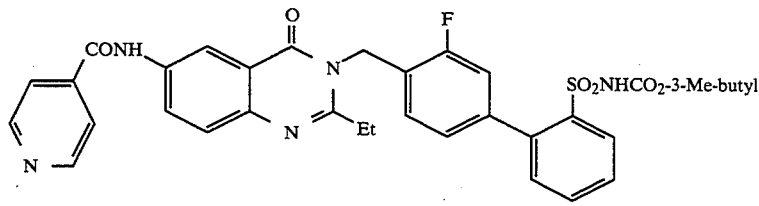

Compound 16 Table 1

The solution of the product of Example 42 (40 mg, 7.07 mmol) and isonicotinoyl chloride hydrochloride (20 mg, 10.2 mmol) in pyridine (1.0 ml) was stirred at room temp for 2 hr. The solvent was removed under reduced pressure and the product was isolated by radial chromatography over silica gel eluting with hexane/ethyl acetate/acetic acid-5/5/1.

$^1$H-NMR (CDCl$_3$/CD$_3$OD-2/1): σ 0.76 (t, J=6.2 Hz, 6H), 1.26–1.50 (m, 5H), 2.80 (q, J=7.4 Hz, 2H), 5.32 (s, 2H), 6.90 (t, J=7.8 Hz, 1H), 6.99–7.10 (m, 2H), 7.25 (dd, J=7.2, 1.6 Hz, 1H), 7.50–7.65 (m, 2H), 7.72 (d, J=8.8 Hz, 1H), 7.87–7.90 (m, 2H), 8.18 (dd, J=7.6, 2.0 Hz, 1H), 8.38 (dd, J=9.0, 2.4 Hz, 1H), 8.50 (d, J=2.0 Hz, 1H), 8.65 (br.s, 2H).

What is claimed is:

1. A compound structural formula (I):

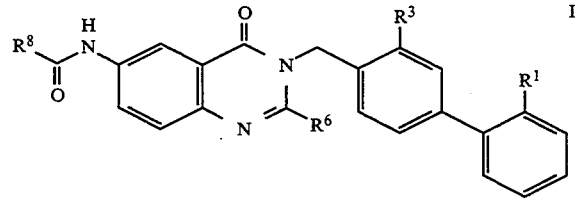

or a pharmaceutically acceptable salt thereof, wherein:

$R^1$ is —SO$_2$NHCO$_2$R$^{23}$;

$R^3$ is
 (a) halogen (Cl, Br, I, F),
 (b) C$_1$–C$_4$ alkyl, or
 (c) CF$_3$;

$R^6$ is straight chain C$_1$–C$_4$ alkyl;

$R^8$ is (a) $R^{23'}$, or
(b) $NR^{24}R^{23'}$;

$R^{23}$ and $R^{23'}$ are independently
  (a) aryl, wherein aryl is defined as phenyl or naphthyl unsubstituted or substituted with one or two substituents selected from the group consisting of: halogen (Cl, Br, I, F), $N(R^{24})_2$, $CO_2R^{24}$, $C_1$-$C_4$ alkyl, $C_1$-$C_4$ alkoxyl, $NO_2$, $CF_3$, $C_1$-$C_4$ alkylthio, OH, —$SO_2N(R^{24})_2$, $C_3$-$C_7$ cycloalkyl, $C_3$-$C_{10}$-alkenyl and $S(O)_n(C_1$-$C_4$ alkyl); where n=1 or 2,
  (b) heteroaryl, wherein heteroaryl is an unsubstituted or mono-or disubstituted heteroaromatic 5- or 6-membered ring which can contain one or two heteroatoms selected from the group consisting of N, O and S and wherein the substituents are members selected from the group consisting of —OH, —SH, $C_1$-$C_4$ alkyl, $C_1$-$C_4$ alkoxy, $CF_3$, halogen (Cl, Br, I, F) and $NO_2$,
  (c) $C_3$-$C_7$ cycloalkyl,
  (d) $C_1$-$C_6$ alkyl which is unsubstituted or substituted with a substituent selected from the group consisting of aryl as defined above, heteroaryl as defined above, —OH, —SH, $C_1$-$C_4$ alkyl, —$O(C_1$-$C_4$ alkyl), $C_3$-$C_7$ cycloalkyl, —$S(O)_n($-$C_1$-$C_4$ alkyl), —$CF_3$, halogen (Cl, Br, F, I), —$NO_2$, —$CO_2H$, $CO_2$—$C_1$-$C_4$ alkyl, —$NH_2$, —$NH(C_1$-$C_4$ alkyl), —$N(C_1$-$C_4$ alkyl)$_2$, or
  (e) perfluoro-$C_1$-$C_4$ alkyl;

$R^{24}$ is
  (a) H,
  (b) $C_1$-$C_6$ alkyl, which is unsubstituted or substituted with aryl as defined above or heteroaryl as defined above, or
  (c) aryl; and $R^{23'}$ and $R^{24}$ when taken together may form a morpholine or piperazine ring, wherein the piperazine ring may be substituted on the nitrogen with $C_1$-$C_4$ alkyl or $C_1$-$C_4$ acyl.

2. The compound of Formula I as recited in claim 1,

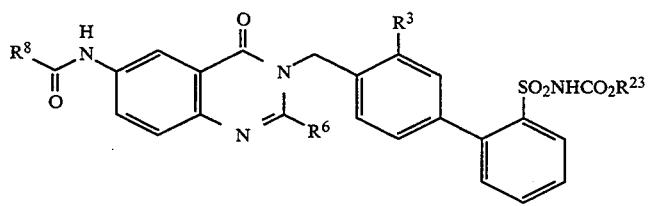

or a pharmaceutically acceptable salt thereof, wherein
$R^3$ is
  (a) F,
  (b) Me, or
  (c) $CF_3$;
$R^6$ is straight chain $C_1$-$C_4$-alkyl;

$R^8$ is $R^{23'}$;
$R^{23'}$ is
  (a) aryl, wherein aryl is defined as phenyl or naphthyl unsubstituted or substituted with one or two substituents selected from the group consisting of: halogen (Cl, Br, I, F), $N(R^{24})_2$, $CO_2R^{24}$, $C_1$-$C_4$ alkyl, $C_1$-$C_4$ alkoxyl, $NO_2$, $CF_3$, $C_1$-$C_4$-alkylthio, OH, —$SO_2N(R^{24})_2$, $C_3$-$C_7$ cycloalkyl, $C_3$-$C_{10}$ alkenyl and $S(O)_n(C_1$-$C_4$ alkyl); where n=1 or 2,
  (b) heteroaryl, wherein heteroaryl is an unsubstituted or mono-or disubstituted heteroaromatic 5- or 6-membered ring which can contain one or two heteroatoms selected from the group consisting of N, O and S and wherein the substituents are members selected from the group consisting of —OH, —SH, $C_1$-$C_4$ alkyl, $C_1$-$C_4$ alkoxy, $CF_3$, halogen (Cl, Br, I, F) and $NO_2$,
  (c) $C_1$-$C_6$ alkyl which is unsubstituted or substituted with a substituent selected from the group consisting of aryl as defined above, heteroaryl as defined above, —OH, —SH, $C_1$-$C_4$ alkyl, —$O(C_1$-$C_4$ alkyl), $C_3$-$C_7$ cycloalkyl, —$CF_3$, halogen (Cl, Br, F, I), —$N(C_1$-$C_4$-alkyl)$_2$, or $C_3$-$C_7$ cycloalkyl; and $R^{23}$ is
  (a) $C_1$-$C_6$ alkyl, unsubstituted or substituted with a substituent selected from the group consisting of: aryl as defined above, heteroaryl as defined above, $C_1$-$C_4$ alkyl, $CF_3$, —$O(C_1$-$C_4$ alkyl), $C_3$-$C_7$ cycloalkyl, or
  (b) perfluoro-$C_1$-$C_4$ alkyl.

3. The compound of claim 1 of structural formula (I):

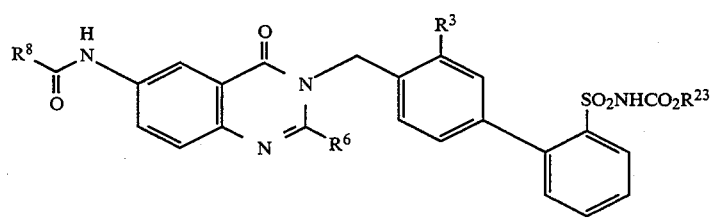

wherein the substituents are as recited in the table below:

| $R^{23}$ | $R^3$ | $R^6$ | $R^8$ |
|---|---|---|---|
| iPn | F | Pr | Ph |
| iPn | F | Pr | -2-furoyl |
| iPn | F | Bu | Et |
| iPn | F | Bu | Pr |
| iPn | F | Pr | $CH_2OCH_2CH_3$ |
| iPn | F | Et | -2-furoyl |
| iPn | F | Et | Ph |
| iPn | F | Et | -3-pyridyl |
| iPn | F | Et | -4-pyridyl |
| iPn | F | Et | -2-pyridyl |

-continued

| R²³ | R³ | R⁶ | R⁸ |
|---|---|---|---|
| (CH₂)₂cPr | F | Et | Ph |
| (CH₂)₂cPr | F | Et | -2-furoyl. |

4. The compound of claim 1 of the structural formula I:

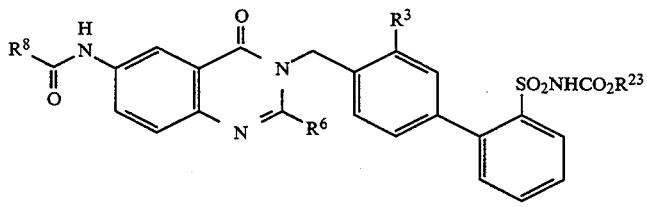

or a pharmaceutically acceptable salt thereof, wherein:
R³ is
  (a) F,
  (b) Me, or
  (c) CF₃;
R⁶ is straight chain $C_1$–$C_4$-alkyl;
R⁸ is NR²⁴R²³';
R²³' is $C_1$–$C_6$ alkyl which is unsubstituted or substituted with a substituent selected from the group aryl, heteroaryl, $C_1$–$C_4$ alkyl, —O($C_1$–$C_4$ alkyl), CF₃, NH($C_1$–$C_4$ alkyl), N($C_1$–$C_4$ alkyl)₂, $C_3$–$C_7$ cycloalkyl;
R²³ is
  (a) $C_1$–$C_6$-alkyl, unsubstituted or substituted with a substituent selected from the group consisting of: aryl as defined above, heteroaryl as defined above, $C_1$–$C_4$ alkyl, CF₃, —O($C_1$–$C_4$ alkyl), $C_3$–$C_7$ cycloalkyl, or
  (b) perfluoro-$C_1$–$C_4$-alkyl;
R²⁴ is
  (a) $C_1$–$C_6$ alkyl which is unsubstituted or substituted with aryl or heteroaryl, or
  (b) H; and
R²³' and R²⁴ when taken together may form a morpholine or piperazine ring, wherein the piperazine ring may be substituted on the nitrogen with $C_1$–$C_4$ alkyl or $C_1$–$C_4$ acyl.

5. The compound of claim 4 of structural formula:

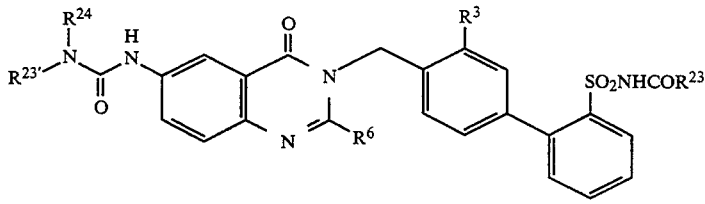

wherein the substituents are as recited in the table below:

| R²³ | R³ | R⁶ | R²³' | R²⁴ |
|---|---|---|---|---|
| iPn | Me | Pr | iPr | H |
| Bu | Me | Pr | iPr | H |
| Bu | F | Pr | iPr | H |
| iPn | F | Pr | iPr | H |
| iPn | Me | Pr | iPr | H |
| Bu | F | Bu | iPr | Me |
| iPn | F | Pr | iPr | H |
| (CH₂)₂cPr | F | Bu | iPr | Me |
| (CH₂)₂cPr | F | Et | Et | H |
| Me | F | Et | Et | H |
| iPn | F | Pr | | morpholino |
| iPn | F | Bu | iPr | Me |
| iPn | F | Et | iPr | Me |
| iPn | F | Et | | morpholino |
| Bu | F | Et | | morpholino |
| iPn | F | Bu | piperazinyl-4-methyl | |
| Bu | F | Et | iPr | Me |
| (CH₂)₂tBu | F | Pr | iPr | H |
| tBu | F | Pr | iPr | H |
| iPr | F | Pr | Me | Me |
| iHx | F | Et | | morpholino |
| iPn | F | Et | Me | Me |
| (CH₂)₂cPr | F | Et | iPr | H |
| (CH₂)₂cPr | F | Et | iPr | Me |
| iPn | F | Me | iPr | H |
| iPn | F | Me | iPr | Me |
| (CH₂)₂cPr | F | Me | Me | Me |
| iBu | F | Et | iPr | Me |
| iPn | F | Et | iPr | Me. |

6. A compound of structural formula:

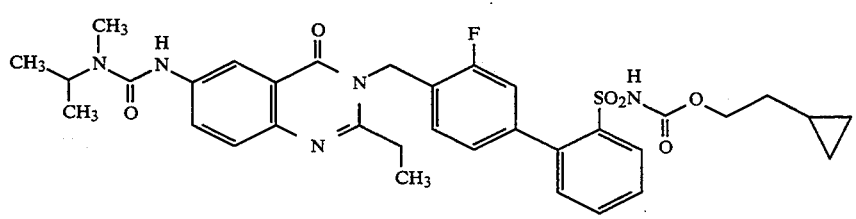

or a pharmaceutically acceptable salt thereof.

7. A compound of structural formula:

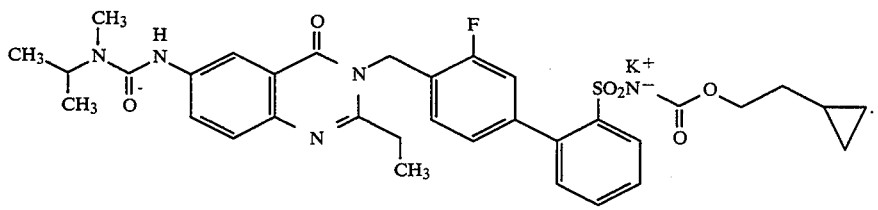

8. A pharmaceutical composition useful in the treatment of hypertension which comprises a pharmaceutically acceptable carrier and a pharmaceutically effective amount of a compound of claim 1.

9. A method of treating hypertension which comprises administering to a patient in need of such treatment a pharmaceutically effective amount of a compound of claim 1.

10. An ophthalmological formulation for the treatment of ocular hypertension comprising an ophthalmologically acceptable carrier and an effective ocular antihypertensive amount of a compound of claim 1.

11. A method of treating ocular hypertension comprising administering to a patient in need of such treatment an effective ocular antihypertensive amount of a compound of claim 1.

12. A method of treating restenosis comprising the administration to a patient in need of such treatment of an effective restenosis inhibiting amount of a compound of claim 1.

* * * * *